(12) United States Patent
Fanelli et al.

(10) Patent No.: US 12,414,771 B2
(45) Date of Patent: Sep. 16, 2025

(54) SURGICAL STAPLER ANVIL HAVING STAPLE FORMING POCKETS WITH LATERALLY VARYING ORIENTATIONS

(71) Applicant: Cilag GmbH International, Zug (CH)

(72) Inventors: Nicholas Fanelli, Morrow, OH (US);
Kevin M. Fiebig, Cincinnati, OH (US);
Jeffery D. Bruns, Cincinnati, OH (US);
John K. Bruce, Morrow, OH (US);
Frederick E. Shelton, IV, Hillsboro, OH (US); John W. Stodghill, Cincinnati, OH (US); Shannon L. Jones, Cincinnati, OH (US); Pierre R. Mesnil, Newport, KY (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/588,269

(22) Filed: Feb. 27, 2024

(65) Prior Publication Data
US 2024/0341761 A1 Oct. 17, 2024

Related U.S. Application Data

(60) Provisional application No. 63/459,739, filed on Apr. 17, 2023.

(51) Int. Cl.
*A61B 17/072* (2006.01)
(52) U.S. Cl.
CPC .............. *A61B 17/07207* (2013.01); *A61B 2017/07264* (2013.01); *A61B 2017/07271* (2013.01); *A61B 2017/07285* (2013.01)
(58) Field of Classification Search
CPC ................................................ A61B 17/07207
See application file for complete search history.

(56) References Cited

U.S. PATENT DOCUMENTS

| 8,008,598 B2 | 8/2011 | Whitman et al. |
| 8,453,914 B2 | 6/2013 | Laurent et al. |
| 8,636,193 B2 * | 1/2014 | Whitman ............. A61B 17/072 227/181.1 |

(Continued)

FOREIGN PATENT DOCUMENTS

| CN | 116919502 A | 10/2023 |
| WO | WO 2022/200977 A1 | 9/2022 |
| WO | WO 2023/067458 A1 | 4/2023 |

OTHER PUBLICATIONS

U.S. Appl. No. 18/588,094.
U.S. Appl. No. 18/588,147.
U.S. Appl. No. 18/588,175.
U.S. Appl. No. 18/588,206.
U.S. Appl. No. 18/588,240.
U.S. Appl. No. 18/588,684.
U.S. Appl. No. 18/758,887.

(Continued)

*Primary Examiner* — Nathaniel C Chukwurah
(74) *Attorney, Agent, or Firm* — Frost Brown Todd LLC

(57) ABSTRACT

An apparatus includes a jaw body, an anvil surface defined by the jaw body, and an elongate slot extending through the anvil surface and along a longitudinal axis of the jaw body. The apparatus further includes a first longitudinal row of staple forming pockets disposed on the anvil surface and configured to form a plurality of first staples such that first legs of each formed first staple are laterally aligned with each other. The apparatus also includes a second longitudinal row of staple forming pockets disposed on the anvil surface laterally outwardly of the first longitudinal row of staple forming pockets relative to the longitudinal axis, and configured to form a plurality of second staples such that second legs of each formed second staple skew laterally away from a second crown of the respective formed second staple.

20 Claims, 17 Drawing Sheets

(56) References Cited

U.S. PATENT DOCUMENTS

| | | | |
|---|---|---|---|
| 9,186,142 | B2 | 11/2015 | Fanelli et al. |
| 9,717,497 | B2 | 8/2017 | Zerkle et al. |
| 9,808,248 | B2 | 11/2017 | Hoffman |
| 9,839,421 | B2 | 12/2017 | Zerkle et al. |
| 10,092,292 | B2 | 10/2018 | Boudreaux et al. |
| 10,130,359 | B2 | 11/2018 | Hess et al. |
| 10,285,705 | B2 | 5/2019 | Shelton, IV et al. |
| 10,682,138 | B2 | 6/2020 | Shelton, IV et al. |
| 10,835,246 | B2 | 11/2020 | Shelton, IV et al. |
| 11,229,433 | B2 | 1/2022 | Schings et al. |
| 2011/0084113 | A1* | 4/2011 | Bedi ................. A61B 17/0644 227/178.1 |
| 2011/0226837 | A1* | 9/2011 | Baxter, III ........... A61B 17/064 227/175.1 |
| 2014/0239037 | A1* | 8/2014 | Boudreaux ...... A61B 17/07207 227/175.1 |
| 2016/0089137 | A1 | 3/2016 | Hess et al. |
| 2018/0132849 | A1 | 5/2018 | Miller et al. |
| 2022/0015760 | A1 | 1/2022 | Beardsley et al. |
| 2023/0121835 | A1 | 4/2023 | Estera et al. |
| 2023/0132138 | A1* | 4/2023 | Stokes ............... A61B 17/0686 227/180.1 |

OTHER PUBLICATIONS

International Search Report and Written Opinion dated May 31, 2024, for International Application No. PCT/IB2024/053663, 17 pages.

U.S. Appl. No. 18/758,887, entitled "Sled Retention and Alignment Features for Surgical Stapler," filed Jun. 28, 2024.

U.S. Appl. No. 18/588,094, entitled "Incompatible Staple Cartridge Use Prevention Features for Surgical Stapler," filed Feb. 27, 2024.

U.S. Appl. No. 18/588,147, entitled "Surgical Stapler Cartridge Having Intermediate Raised Tissue Engagement Protrusions," filed Feb. 27, 2024.

U.S. Appl. No. 18/588,175, entitled "Surgical Stapler Cartridge Having Tissue Engagement Protrusions with Enlarged Engagement Surface," filed Feb. 27, 2024.

U.S. Appl. No. 18/588,206, entitled "Surgical Stapler Cartridge Having Raised Surface to Promote Buttress Adhesion," filed Feb. 27, 2024.

U.S. Appl. No. 18/588,240, entitled "Surgical Stapler Cartridge Having Cartridge Retention Features," filed Feb. 27, 2024.

U.S. Appl. No. 18/588,684, entitled "Method of Surgical Stapling," filed Feb. 27, 2024.

* cited by examiner

SURGICAL STAPLER ANVIL HAVING STAPLE FORMING POCKETS WITH LATERALLY VARYING ORIENTATIONS

PRIORITY

This application claims the benefit of U.S. Pat. App. No. 63/459,739, entitled "Surgical Stapler Anvil Having Staple Forming Pockets with Laterally Varying Orientations," filed Apr. 17, 2023, the disclosure of which is incorporated by reference herein.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion or other type of body portion, which is manipulated by the clinician or robotic operator. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Such endoscopic surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to an organ, such as a lung. For instance, the vessels leading to an organ may be severed and closed by a stapler before removal of the organ from the thoracic cavity. Of course, surgical staplers may be used in various other settings and procedures.

Staples formed by such surgical staplers may have a two-dimensional ("2D") formed configuration in which the legs of each staple are formed such that the leg tips are laterally aligned with each other, thus providing each formed staple with a planar shape. Such 2D formed configurations of staples may generally provide tight tissue compression, but may generally provide sub-optimal leak path resistance. Alternatively, the staples formed by such surgical staplers may have a three-dimensional ("3D") formed configuration in which the legs of each staple are formed such that the leg tips are laterally offset from each other, thus providing each formed staple with a non-planar shape. Such 3D formed configurations of staples may generally provide improved leak path resistance, but may generally provide loose tissue compression. The surgical staplers of the present disclosure seek to strike a desired balance between achieving tight tissue compression and optimal leak path resistance.

While various kinds of surgical staplers and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate examples of the invention, and, together with the general description of the invention given above, and the detailed description of the examples given below, serve to explain the principles of the present invention.

Figure 1:
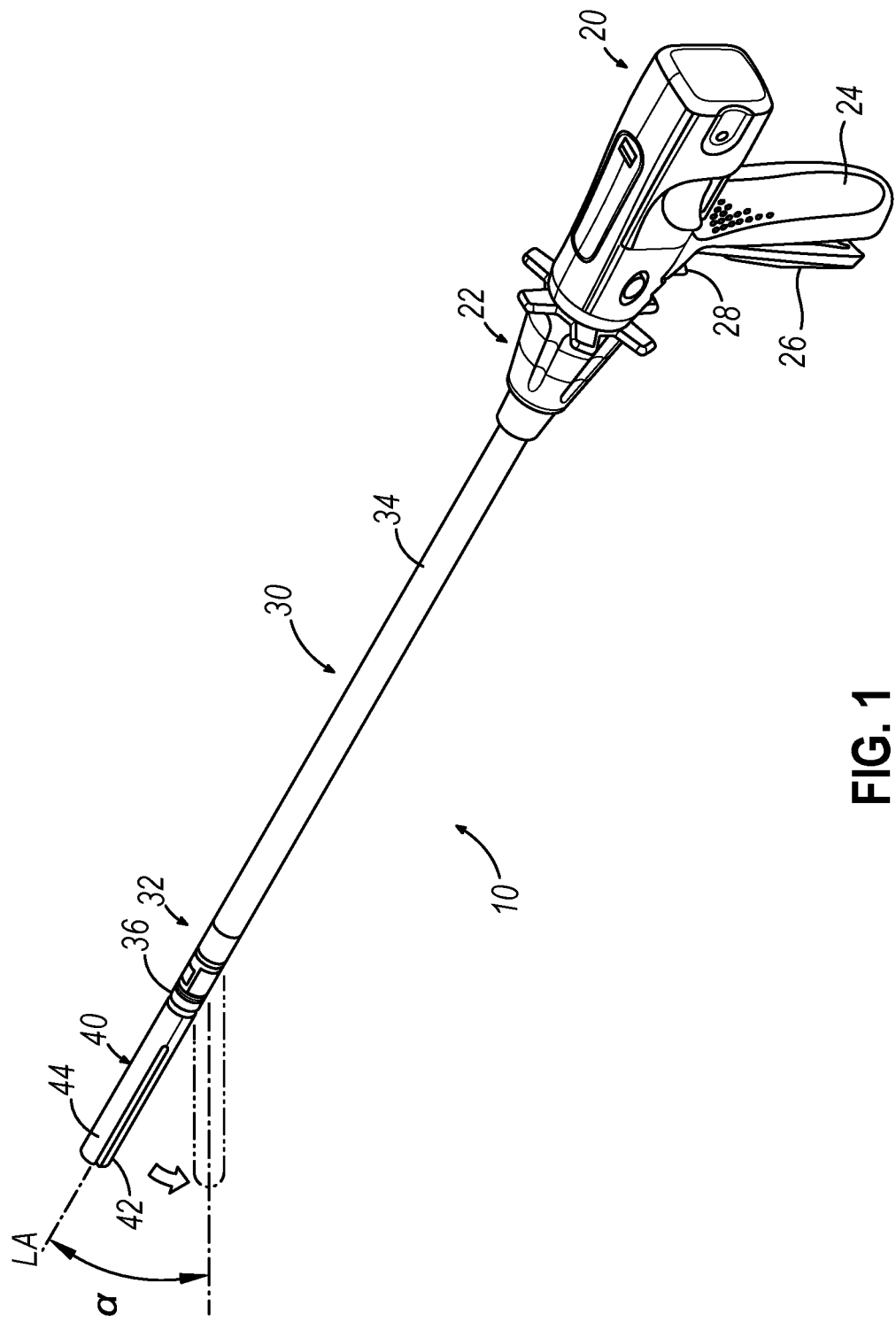
FIG. 1 depicts a perspective view of an example of a surgical stapler.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

Furthermore, the terms "about," "approximately," "substantially," and the like as used herein in connection with any numerical values, ranges of values, and/or geometric/positional quantifications are intended to encompass the exact value(s) referenced as well as a suitable tolerance that enables the referenced feature or combination of features to function for the intended purpose described herein. For example, "substantially parallel" encompasses nominally parallel structures.

As used herein in connection with any examples of end effector jaw tips, a tip described as "angled," "bent," or "curved" encompasses tip configurations in which a longitudinal path (e.g., linear or arcuate) along which the tip extends is non-coaxial and non-parallel with a longitudinal axis of the jaw body; particularly, configurations in which the longitudinal tip path extends distally toward the opposing jaw. Conversely, a tip described as "straight" encompasses tip configurations in which a longitudinal axis of the tip is substantially parallel or coaxial with the longitudinal axis of the jaw body.

I. Overview of Surgical Stapler Features

FIGS. 1-6 depict an illustrative surgical stapler (10) that is sized for insertion through a trocar cannula or a surgical incision (e.g., thoracotomy, etc.) to a surgical site in a patient for performing a surgical procedure. Surgical stapler (10) includes a body exemplified as a handle assembly (20), a shaft (30) that extends distally from handle assembly (20) along a longitudinal axis (LA) and distally terminates at an articulation joint (32), and an end effector (40) operatively coupled with shaft (30) via articulation joint (32).

Once end effector (40) and articulation joint (32) are inserted distally through the cannula passageway of a trocar, articulation joint (32) may be remotely articulated, as depicted in phantom in FIG. 1, by an articulation control exemplified as a rotatable knob (22) of handle assembly (20), such that end effector (40) may be deflected from the longitudinal axis (LA) at a desired angle ($\alpha$). Articulation joint (32) and related features for manipulating articulation joint (32) may be further configured in accordance with the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein in its entirety.

End effector (40) includes a lower jaw exemplified as a cartridge jaw (42) configured to removably receive a staple cartridge (70) (also referred to as a "reload"), and an upper jaw exemplified as an anvil jaw (44) (also referred to as an "anvil") that pivots relative to cartridge jaw (42) to clamp tissue therebetween. In other versions, end effector (40) may be alternatively configured such that cartridge jaw (42) pivots relative to anvil jaw (44). Unless otherwise described, the term "pivot" (and variations thereof) as used herein in connection with the relative motion between jaws (42, 44) encompasses but is not necessarily limited to pivotal movement about a fixed axis. For instance, in some versions, anvil jaw (44) may pivot about an axis that is defined by a pin (or similar feature) that slidably translates along an elongate slot or channel as anvil jaw (44) moves toward cartridge jaw (42). Such translation may occur before, during, or after the pivotal motion. It should therefore be understood that such combinations of pivotal and translational movement are encompassed by the term "pivot" and variations thereof as used herein with reference to the relative motion between jaws (42, 44).

As shown in FIG. 1, handle assembly (20) includes a pistol grip (24) and a closure trigger (26). Closure trigger (26) is pivotable toward pistol grip (24) to cause clamping, or closing, of anvil jaw (44) toward cartridge jaw (42) of end effector (40). Such closing of anvil jaw (44) is provided through a closure tube (34) and a closure ring (36) of shaft (30), which both longitudinally translate relative to handle assembly (20) in response to pivoting of closure trigger (26) relative to pistol grip (24). Closure tube (34) extends along the length of shaft (30); and closure ring (36) is positioned distal to articulation joint (32). Articulation joint (32) is operable to transmit longitudinal movement from closure tube (34) to closure ring (36) to actuate anvil jaw (44) relative to cartridge jaw (42).

Handle assembly (20) also includes a firing trigger (28). An elongate actuator (not shown) extends longitudinally through shaft (30) and transmits a longitudinal firing motion from handle assembly (20) to a firing member (also referred to herein as a firing driver) exemplified as a firing beam (46) in response to actuation of firing trigger (28). As a result, firing beam (46) translates distally through a firing stroke to cause stapling and severing of tissue clamped by end effector (40), as will be described in greater detail below. Though not shown, handle assembly (20) may further include a motor operable to actuate such firing assembly components of surgical stapler (10) in response to actuation of firing trigger (28) by a user, for example as disclosed in U.S. Pat. No. 8,453,914, entitled "Motor-Driven Surgical Cutting Instrument with Electric Actuator Directional Control Assembly," issued Jun. 4, 2013, the disclosure of which is incorporated by reference herein in its entirety.

As shown in FIGS. 2-5, firing beam (46) includes a proximal beam portion (48) and a distal knife portion (50), where distal knife portion (50) may be integrally formed with a distal end of proximal beam portion (48), or separately formed and thereafter securely affixed to the distal end of proximal beam portion (17). Distal knife portion (50) includes a transversely oriented upper protrusion exemplified as an upper pin (52), a transversely oriented lower protrusion exemplified as a cap (54), a transversely oriented middle protrusion exemplified as a middle pin (56), and a distally presented cutting edge (58). Upper pin (52) is slidable within a longitudinal anvil jaw slot (62) of anvil jaw (44) and cap (54) is slidable along a lower surface of cartridge jaw (42) defined by a longitudinal cartridge jaw slot (64). Middle pin (56) is slidable along a top surface of cartridge jaw (42) and cooperates with cap (54) to stabilize and guide distal knife portion (50) along a longitudinal firing stroke. Firing beam (46) may be further configured and operable in accordance with the teachings of U.S. Pat. No. 9,717,497, entitled "Lockout Feature for Movable Cutting Member of Surgical Instrument," issued Aug. 1, 2017, the disclosure of which is incorporated by reference herein in its entirety.

Figure 2:
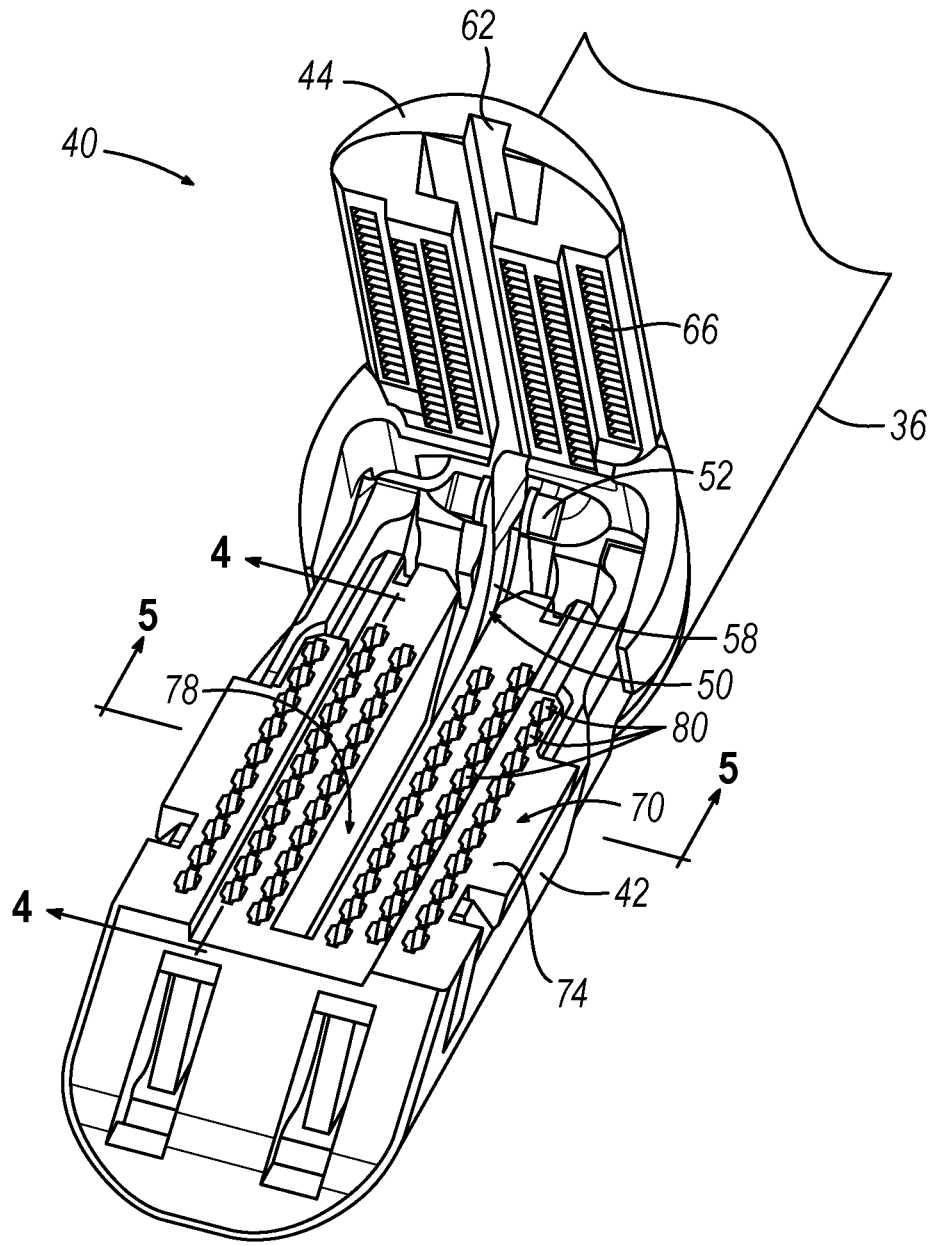
FIG. 2 depicts a perspective view of an end effector of the surgical stapler of FIG. 1, shown in an open state.
Figure 3:
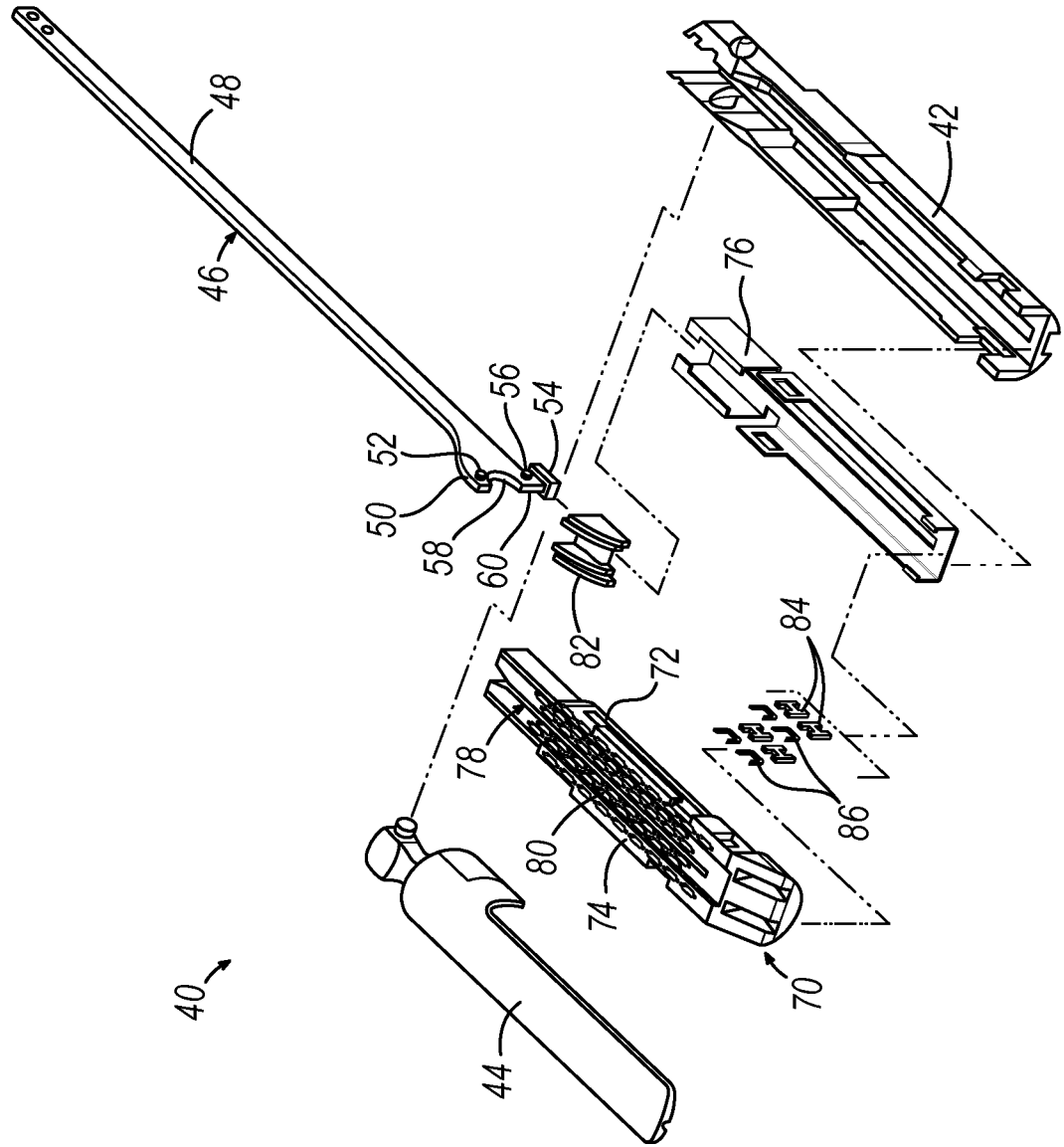
FIG. 3 depicts an exploded perspective view of the end effector of FIG. 2.

FIG. 2 shows anvil jaw (44) pivoted to an open state with firing beam (46) proximally positioned, which permits an unspent (i.e., unfired) staple cartridge (70) to be removably installed into a channel of cartridge jaw (42). As best seen in FIGS. 2-3, staple cartridge (70) includes a cartridge body (72) that presents an upper deck (74) defining a first stapling surface, and a lower pan (76) (also referred to as a "tray") coupled to an underside of cartridge body (72). A vertical knife slot (78) extends longitudinally through cartridge body (72) and is configured to slidably receive distal knife portion (50) of firing beam (46). In the present version, three rows of cartridge pockets (80) (also referred to as "staple openings," "staple apertures," or "staple cavities") are formed through upper deck (74) along each lateral side of knife slot (78).

Figure 4A:
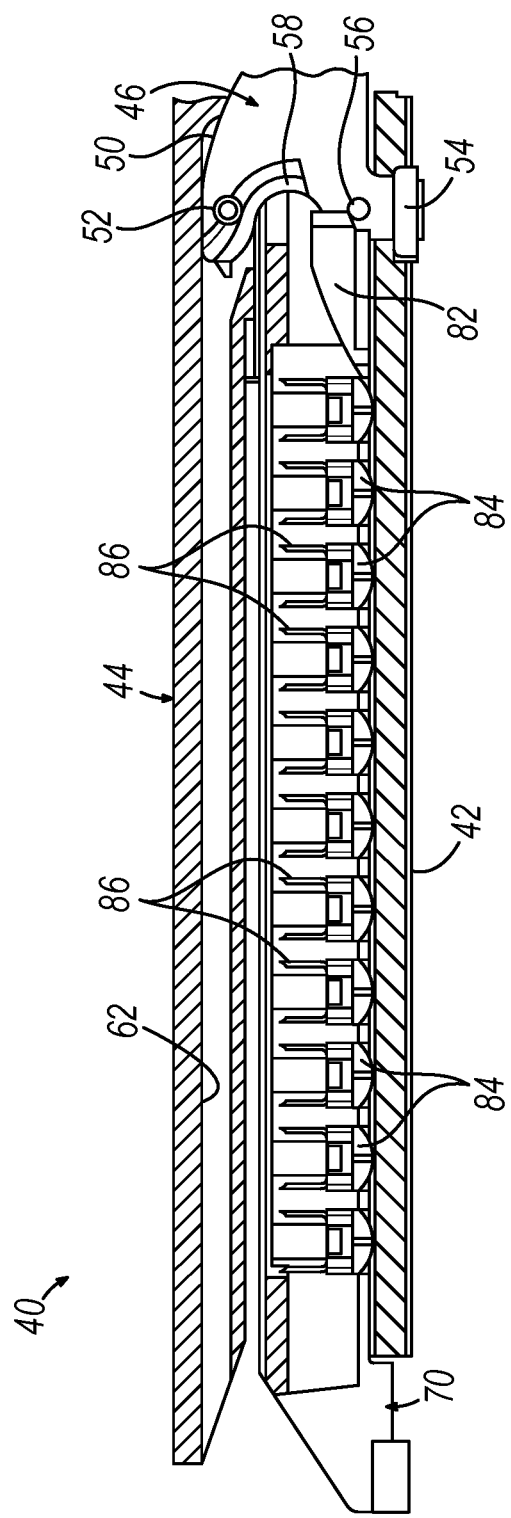
FIG. 4A depicts a side cross-sectional view of the end effector of FIG. 2, taken along line 4-4 of FIG. 2, showing a firing beam and sled in a proximal unfired position.
Figure 4B:
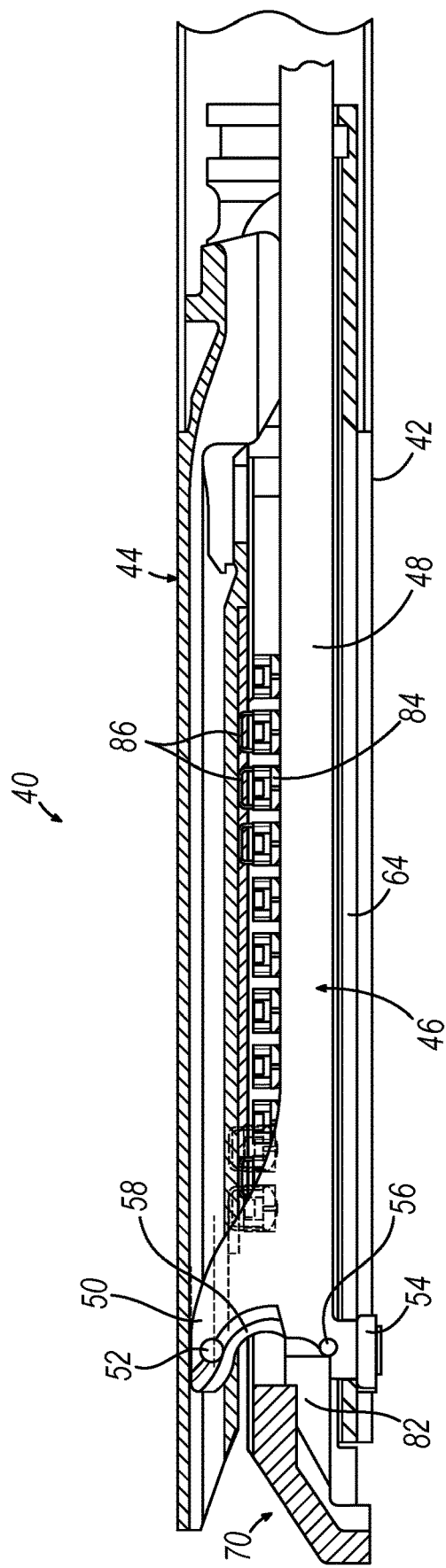
FIG. 4B depicts a side cross-sectional view of the end effector of FIG. 2, taken along line 4-4 of FIG. 2, showing the firing beam and sled in a distal fired position.
Figure 5:
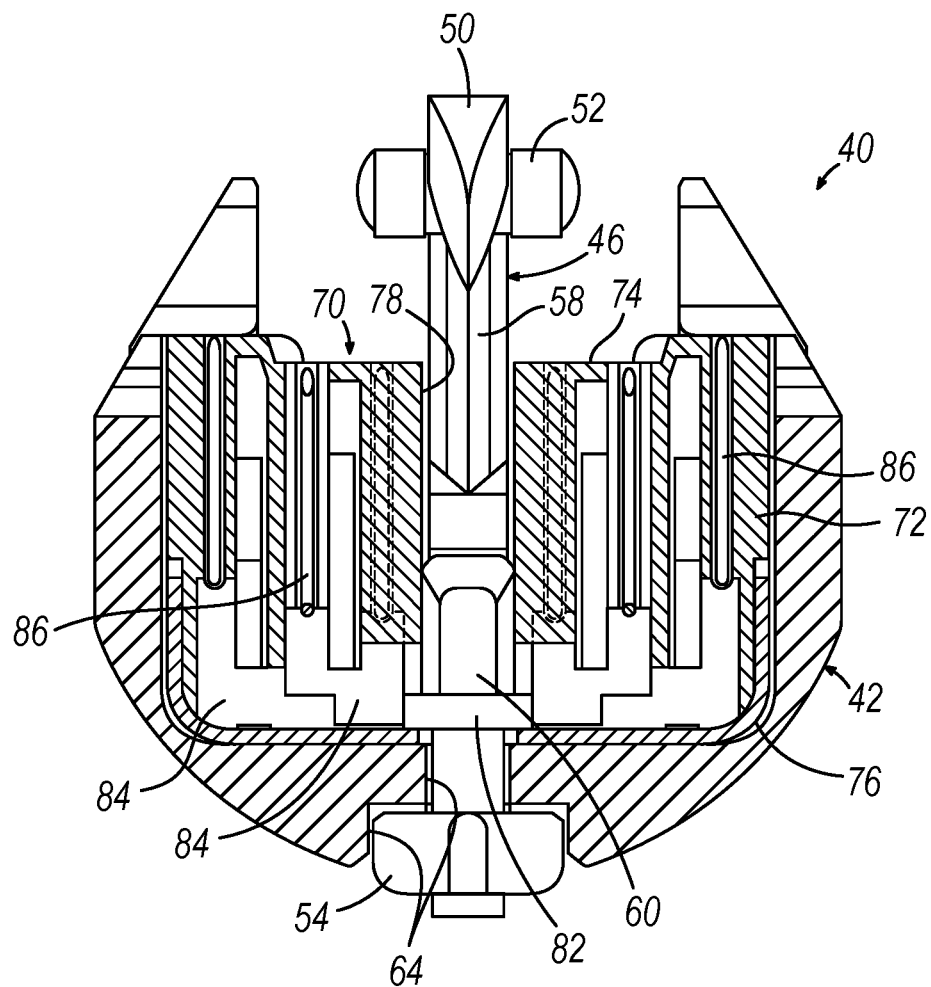
FIG. 5 depicts an end cross-sectional view of the end effector of FIG. 2, taken along line 5-5 of FIG. 2 and omitting an upper anvil jaw, showing further details of a distal knife portion of the firing beam and the sled.

As shown in FIGS. 3-5, staple cartridge (70) further includes a sled (82) (also referred to as a "wedge sled") and a plurality of staple drivers (84) that are movably captured between cartridge body (72) and pan (76). Each staple driver (43) is aligned with and movable vertically within a respective cartridge pocket (51). Staples (86) are positioned within respective cartridge pockets (80) above respective staple drivers (84). During a firing stroke, sled (82) is actuated longitudinally within staple cartridge (70) by distal knife portion (50) from a proximal position shown in FIG. 4A to a distal position shown in FIG. 4B. Angled cam surfaces of sled (82) cam staple drivers (84) vertically upwardly within cartridge pockets (80) to drive staples (86) upwardly above deck (74), thereby ejecting staples (86) from cartridge pockets (80) and toward anvil jaw (44).

More specifically, with end effector (40) closed as shown in FIGS. 4A-4B, firing beam (46) is actuated distally into engagement with anvil jaw (44) by directing upper pin (52) into longitudinal anvil slot (62). A distal end projection (60) (see FIG. 5) of distal knife portion (50) of firing beam (46) engages a proximal end of sled (82) and drives sled (82) distally as distal knife portion (50) is advanced distally through staple cartridge (70) in response to actuation of firing trigger (28). During such firing, distal knife portion (50) advances distally along knife slot (78) of staple cartridge (70) so that cutting edge (58) severs tissue clamped between staple cartridge (70) and anvil jaw (44).

As shown in FIGS. 4A-4B, middle pin (56) and distal end projection (60) together actuate staple cartridge (70) by entering into knife slot (78), driving sled (82) into camming contact with staple drivers (84) to thereby actuate staple drivers (84) upwardly, which in turn drives staples (86) outwardly through cartridge pockets (80), through clamped tissue, and into forming contact with staple forming pockets (66) (see FIG. 2) on a second stapling surface defined by anvil jaw (44). Such stapling of tissue prompted by the camming interaction between sled (82) and staple drivers (84) is performed concurrently with the severing of tissue performed by cutting edge (58). However, it will be appreciated that for each longitudinal section of tissue clamped by end effector (40), staples (86) may be ejected into the tissue slightly before cutting edge (58) severs the tissue to ensure that the tissue is stapled and thus sealed before being severed. FIG. 4B depicts firing beam (46) fully distally translated at the end of a firing stroke after the tissue clamped by end effector (40) has been stapled and severed.

Staple cartridge (70) and anvil jaw (44) may be further configured and operable in accordance with the teachings of U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; U.S. Pat. No. 10,092,292, entitled "Staple Forming Features for Surgical Stapling Instrument," issued Oct. 9, 2018; and/or U.S. Pat. No. 10,130,359, entitled "Method for Forming a Staple," issued Nov. 20, 2018, the disclosure of each of which is incorporated by reference herein in its entirety.

Figure 6:
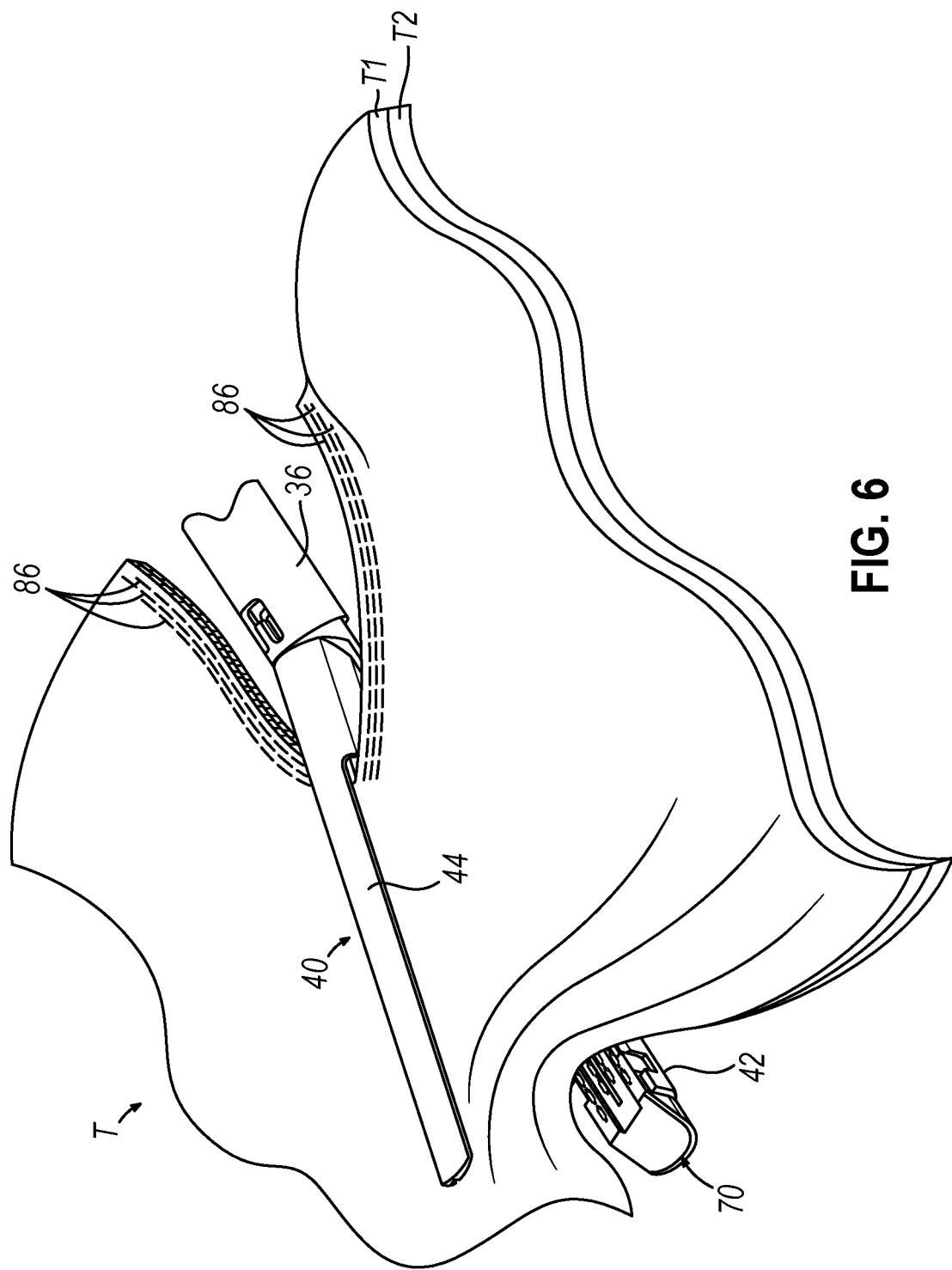
FIG. 6 depicts a perspective view of the end effector of FIG. 3, shown after having been fired once on a first section of tissue and being positioned to clamp and fire on a second section on tissue.
Figure 7:
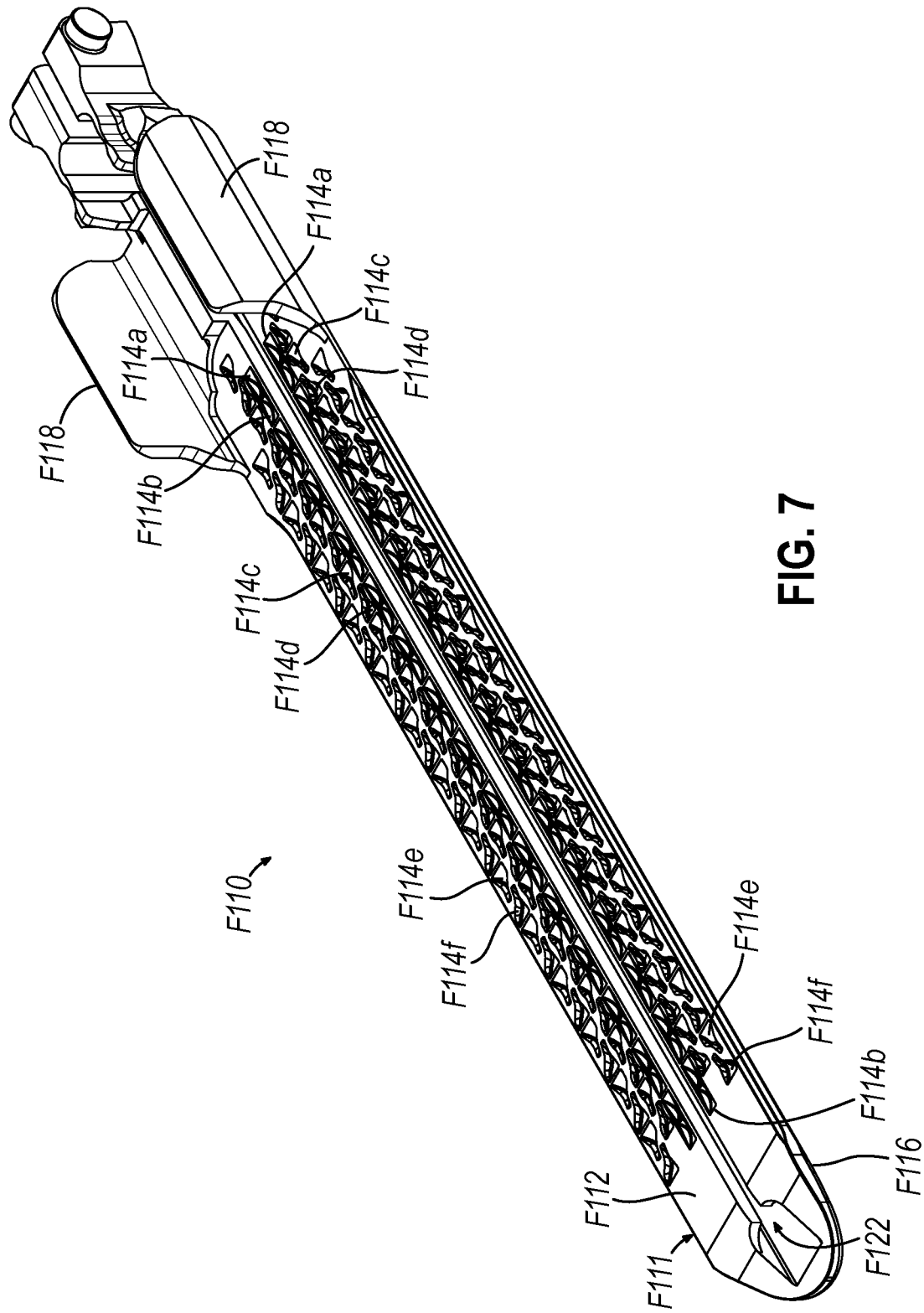
FIG. 7 depicts a perspective view of another example of an upper anvil jaw for use with the end effector of FIG. 2 and having 2D and 3D staple forming pockets.

FIG. 6 shows end effector (40) having been actuated through a single firing stroke on tissue (T) having first and second layers (T1, T2). Cutting edge (58) (see FIGS. 2-5) has cut through tissue (T) while staple drivers (84) have driven three alternating rows of staples (86) through tissue (T) on each side of the cut line produced by cutting edge (58). After the first firing stroke is complete, end effector (40) is withdrawn from the patient, spent staple cartridge (70) is replaced with a new unspent staple cartridge (70), and end effector (40) is then again inserted into the patient to reach the stapling site for further cutting and stapling. This process may be repeated until the desired quantity and pattern of firing strokes across the tissue (T) has been completed.

II. Example of Anvil Having 2D and 3D Staple Forming Pockets

In some instances, it may be desirable to arrange and configure staple forming pockets (66) of anvil jaw (44) to achieve improved sealing of severed tissue, such as by striking a desired balance between achieving tight tissue compression and good leak path resistance. FIGS. 7-10 show an example of an anvil jaw (F110) (also referred to as an "anvil") that may provide such capabilities, and that may be incorporated into end effector (40) in place of anvil jaw (44). Anvil jaw (F110) may be similar to anvil jaw (44) described above, except as otherwise described below. In this regard, anvil jaw (F110) may be configured to pivot relative to cartridge jaw (42) of end effector (40) (or cartridge jaw (42) may be configured to pivot relative to anvil jaw (F110)), to clamp tissue therebetween.

In the example shown, anvil jaw (F110) includes a body (F111) having an interior side that defines an anvil surface (F112) configured to compress tissue and having a plurality of staple forming pockets (F114a, F114b, F114c, F114d, F114e, F114f), and an opposed exterior side defining an exterior surface (F116). Anvil jaw (F110) also includes a pair of tissue stops (F118) that extend downwardly from a proximal portion of anvil jaw (F110) on opposed lateral sides such that tissue stops (F118) extend beyond anvil surface (F112). Tissue stops (F118) are configured to inhibit tissue (T) from advancing too far proximally relative to anvil jaw (F110) when tissue (T) is positioned between anvil jaw (F110) and cartridge jaw (42). More specifically, tissue stops (F118) allow tissue (T) to be proximally advanced in end effector (40) only to a predetermined position to ensure adequate engagement of staples (86a, 86b, 86c) (FIGS. 12-13) with tissue (T) and to ensure that anvil jaw (F110) can pivot to a closed state without binding on tissue (T). Tissue stops (F118) are also configured to limit the lateral rotation of anvil jaw (F110) relative to lower cartridge jaw (42) by engaging lateral side portions of lower cartridge jaw (42). This can be useful for ensuring proper lateral alignment between the more proximally located staples (86a, 86b, 86c) and the corresponding staple forming pockets (F114a, F114b, F114c, F114d, F114e, F114f).

Figure 8:
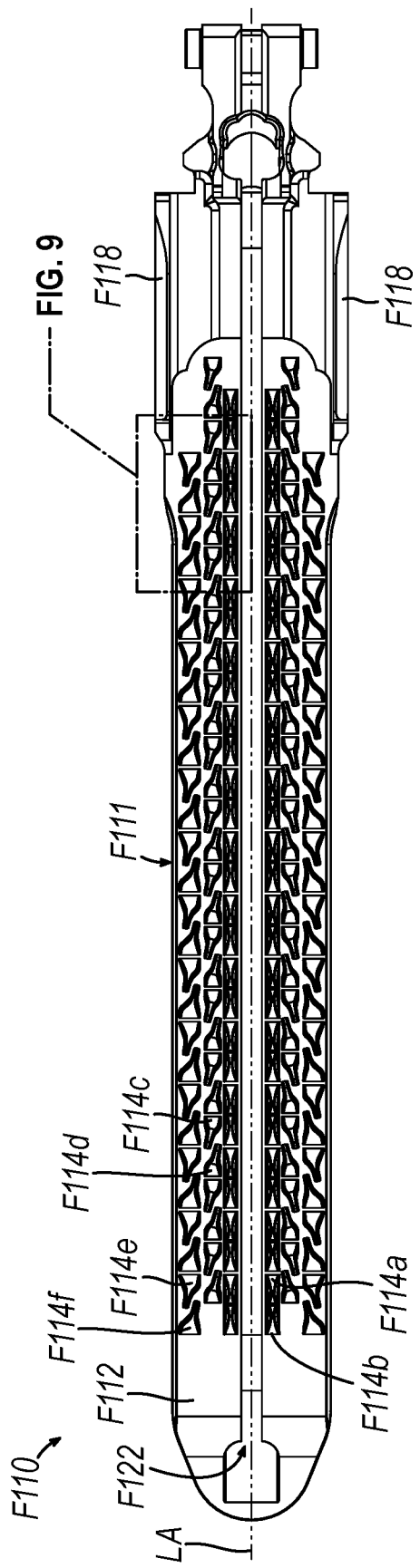
FIG. 8 depicts a bottom plan view of the upper anvil jaw of FIG. 7.

Anvil jaw (F110) further includes an elongate anvil slot (F122) (also referred to herein as a firing driver slot) that extends through anvil surface (F112). As shown in FIG. 8, anvil slot (F122) extends along a longitudinal axis (LA) of anvil jaw (F110). Anvil slot (F122) is configured to slidably receive upper pin (52) of firing beam (46) in a manner similar to that described above in connection with longitudinal anvil slot (62).

In the example shown, staple forming pockets (F114a, F114b, F114c, F114d, F114e, F114f) are arranged in pairs on anvil surface (F112) on each side of anvil slot (F122). Each staple forming pocket (F114a, F114b, F114c, F114d, F114e, F114f) is configured to receive and deform a respective leg of a staple (86a, 86b, 86c) ejected by a staple cartridge (not shown) that is received within lower cartridge jaw (42) when stapler (10) is fired. Accordingly, staple forming pockets (F114a, F114b, F114c, F114d, F114e, F114f) cooperate to form the ejected staples (86a, 86b, 86c) in tissue clamped between lower cartridge jaw (42) and anvil jaw (F110). In the present version, anvil jaw (F110) includes three linear (e.g., straight) rows of staple forming pockets (F114a, F114b, F114c, F114d, F114e, F114f) on each side of anvil slot (F122), though it will be appreciated that anvil jaw (F110) may include various other configurations of staple pockets (F114a, F114b, F114c, F114d, F114e, F114f) in other versions. More particularly, anvil jaw (F110) of the present version includes a laterally inner row of staple forming pockets (F114a, F114b), a laterally intermediate row of staple forming pockets (F114c, F114d), and a laterally outer row of staple forming pockets (F114e, F114f) all formed through the same anvil surface (F112) on each side of anvil slot (F122), with the laterally inner row of staple forming pockets (F114a, F114b) being closest to the longitudinal axis (LA) on the respective side of anvil slot (F122), the laterally outer row of staple forming pockets (F114e, F114f) being farthest from the longitudinal axis (LA) on the respective side of anvil slot (F122), and the laterally intermediate row of staple forming pockets (F114c, F114d) being disposed between the laterally inner row of staple forming pockets (F114a, F114b) and the laterally outer row of staple forming pockets (F114e, F114f) on the respective side of anvil slot (F122).

As described in greater detail below, each row of staple forming pockets (F114a, F114b, F114c, F114d, F114e, F114f) has a unique geometry relative to the other two rows of staple forming pockets (F114a, F114b, F114c, F114d, F114e, F114f) on the same side of the longitudinal axis (LA), such that the configurations and/or orientations of staple forming pockets (F114a, F114b, F114c, F114d, F114e, F114f) vary in the lateral direction. In this manner, each row of staple forming pockets (F114a, F114b, F114c, F114d, F114e, F114f) may be configured to form the corresponding row of staples (86a, 86b, 86c) with a unique configuration relative to the other two rows of staples (86a, 86b, 86c) on the same side of the cut line produced by cutting edge (58).

Figure 9:
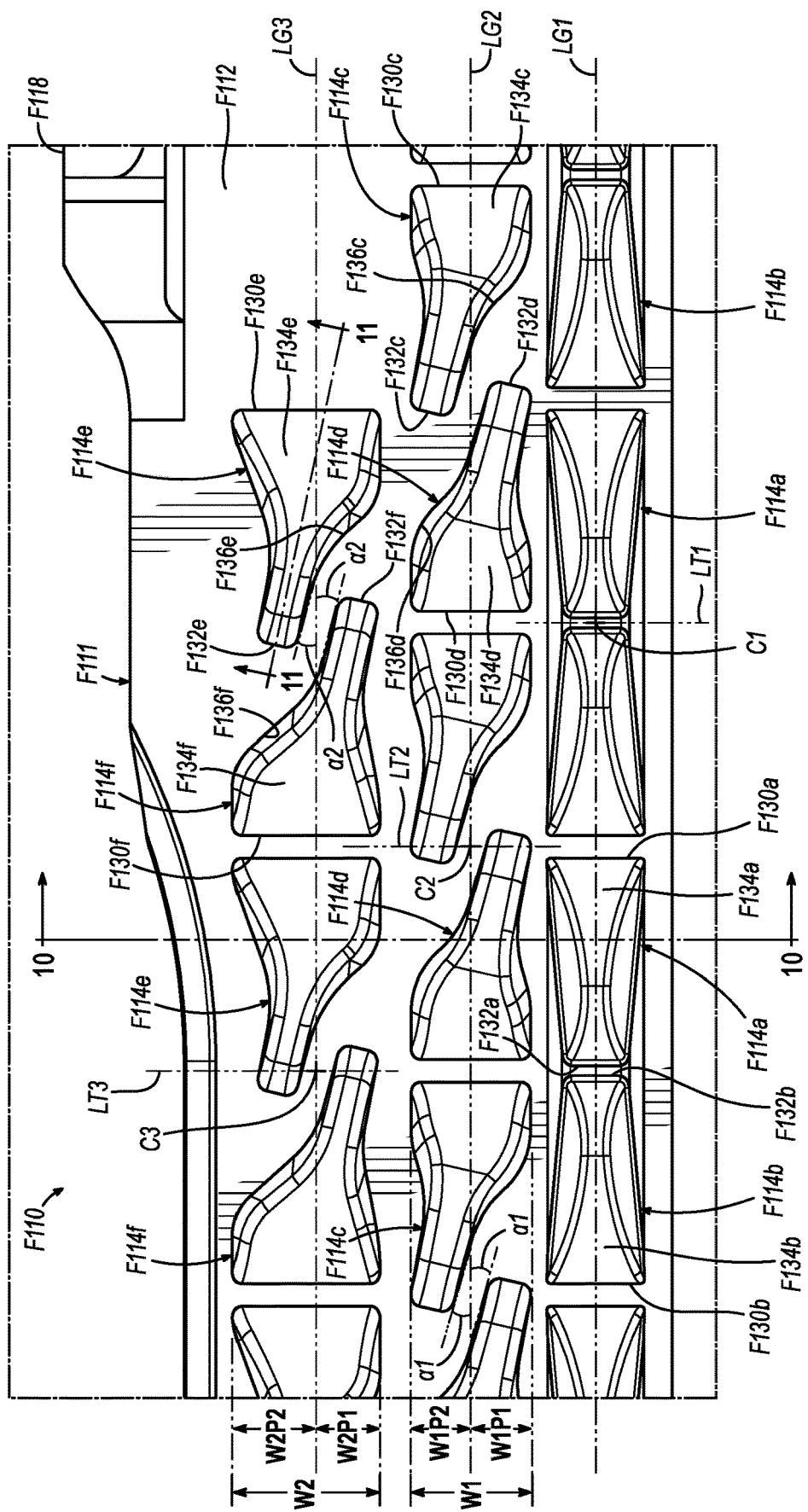
FIG. 9 depicts a magnified view of area 9 of the upper anvil jaw of FIG. 7 as indicated in FIG. 8.

As best shown in FIGS. 8 and 9, staple forming pockets (F114a, F114b, F114c, F114d, F114e, F114f) are arranged in longitudinally adjacent pairs such that each pair is configured to receive and deform the legs of a respective staple (86a, 86b, 86c) and thereby transform the staple (86a, 86b, 86c) into a formed shape when firing beam (46) is actuated distally. More particularly, each proximal, laterally inner staple forming pocket (F114a) is configured to cooperate with the longitudinally adjacent distal, laterally inner staple forming pocket (F114b) to provide the resulting staple (86a) with a two-dimensional B-shape in which the crown and each bent leg of the formed staple (86a) lies in the same plane; each proximal, laterally intermediate staple forming pocket (F114c) is configured to cooperate with the longitudinally adjacent distal, laterally intermediate staple forming pocket (F114d) to provide the resulting staple (86b) with a first three-dimensional formed shape in which the crown and each bent leg of the formed staple (86b) lies in a different plane; and each proximal, laterally outer staple forming pocket (F114e) is configured to cooperate with the longitudinally adjacent distal, laterally outer staple forming pocket (F114f) to provide the resulting staple (86c) with a second three-dimensional formed shape different from the first three-dimensional formed shape in which the crown and each bent leg of the formed staple (86c) lies in a different plane. For example, such first and/or second three-dimensional formed shapes may be provided in accordance with any one or more teachings of U.S. Pat. No. 11,229,433, entitled "Linear Surgical Stapler," issued on Jan. 25, 2022, the disclosure of which is incorporated by reference herein.

As shown in FIG. 9, each individual staple forming pocket (F114a, F114b, F114c, F114d, F114e, F114f) of the present version includes a respective wide entry end (F130a, F130b, F130c, F130d, F130e, F130f) (also referred to as a staple catch area), and a respective narrow exit end (F132a, F132b, F132c, F132d, F132e, F132f) (also referred to as a staple forming area). Each pocket (F114a, F114b, F114c, F114d, F114e, F114f) further includes a respective concave base surface (F134a, F134b, F134c, F134d, F134e, F134f) that extends between the corresponding entry end (F130a, F130b, F130c, F130d, F130e, F130f) and exit end (F132a, F132b, F132c, F132d, F132e, F132f) such that each pocket (F114a, F114b, F114c, F114d, F114e, F114f) has a varying depth along its length.

In the example shown, entry and exit ends (F130a, F130b, F132a, F132b) of laterally inner staple forming pockets (F114a, F114b) extend substantially parallel to the longitudinal axis (LA), with the width of each proximal, laterally inner staple forming pocket (F114a) tapering gradually inwardly in a distal direction from the respective entry end (F130a) to the respective exit end (F132a); and the width of each distal, laterally inner staple forming pocket (F114b) tapering gradually inwardly in a proximal direction from the respective entry end (F130b) to the respective exit end (F132b). Entry ends (F130a, 130b) are each configured to receive and guide a staple leg in an unformed state longitudinally along the respective concave base surface (F134a, F134b) and toward the respective exit end (F132a, F132b) to be deformed. Exit ends (F132a, F132b) are each configured to guide the staple leg in a deformed state in a direction toward lower cartridge jaw (42) and into clamped tissue (T). The exit end (F132a) of each proximal, laterally inner staple forming pocket (F114a) is longitudinally adjacent to the exit end (F132b) of the corresponding longitudinally-paired distal, laterally inner staple forming pocket (F114b). In some versions, the exit ends (F132a, F132b) of longitudinally-paired laterally-inner staple forming pockets (F114a, F114b) may overlap or otherwise directly communicate with each other, such that each longitudinal pair of laterally-inner staple forming pockets (F114a, F114b) may be effectively merged to define a single corresponding laterally-inner staple forming pocket.

When end effector (40) is closed such that each pair of laterally inner pockets (F114a, F114b) is vertically aligned with a corresponding cartridge pocket (not shown) in a laterally inner row of the staple cartridge that is received within lower cartridge jaw (42), each laterally inner pocket (F114a, F114b) is symmetrical about an inner longitudinal centerline (LG1) that extends parallel to the longitudinal axis (LA) through the center points (C1) of the laterally inner cartridge pockets; and each proximal, laterally inner staple forming pocket (F114a) is symmetric relative to the corresponding longitudinally-paired distal, laterally inner staple forming pocket (F114b) about a corresponding lateral centerline (LT1) that extends perpendicular to the longitudinal axis (LA) through the center point (C1) of the corresponding laterally inner cartridge pocket.

In the example shown, entry ends (F130c, F130d) of laterally intermediate staple forming pockets (F114c, F114d) extend substantially parallel to the longitudinal axis (LA), while exit ends (F132c, F132d) of laterally intermediate staple forming pockets (F114c, F114d) extend substantially obliquely relative to the longitudinal axis (LA). In this regard, exit ends (F132c) of proximal, laterally intermediate staple forming pockets (F114c) are oriented laterally outwardly relative to the longitudinal axis (LA) at a first angle ($\alpha 1$), and exit ends (F132d) of distal, laterally intermediate staple forming pockets (F114d) are oriented laterally inwardly relative to the longitudinal axis (LA) at the first angle ($\alpha 1$). A medial portion of each laterally intermediate staple forming pocket (F114c, F114d) located between the respective entry and exit ends (F130c, F130d, F132c, F132d) includes an angled and/or curved sidewall (F136c, F136d) that faces toward the respective entry end (F130c, F130d) and which is longitudinally adjacent to the exit end (F132c, F132d) of the corresponding longitudinally-paired laterally intermediate staple forming pocket (F114c, F114d). Entry ends (F130c, F130d) are each configured to receive and guide a staple leg in an unformed state longitudinally along the respective concave base surface (F134c, F134d) and toward the respective angled sidewall (F136c, F136d) to be deformed. Exit ends (F132c, F132d) are each configured to guide the staple leg in a deformed state in a direction toward lower cartridge jaw (42) and into clamped tissue (T). The exit end (F132c) of each proximal, laterally intermediate staple forming pocket (F114c) is laterally adjacent to, and extends substantially parallel to, the exit end (F132d) of the corresponding longitudinally-paired distal, laterally intermediate staple forming pocket (F114d).

When end effector (40) is closed such that each pair of laterally intermediate pockets (F114c, F114d) is vertically aligned with a corresponding cartridge pocket (not shown) in a laterally intermediate row of the staple cartridge that is received within lower cartridge jaw (42), each laterally intermediate pocket (F114c, F114d) is asymmetrical about an intermediate longitudinal centerline (LG2) that extends parallel to the longitudinal axis (LA) through the center points (C2) of the laterally intermediate cartridge pockets; and each proximal, laterally intermediate staple forming pocket (F114c) is asymmetric relative to the corresponding longitudinally-paired distal, laterally intermediate staple forming pocket (F114d) about a corresponding lateral centerline (LT2) that extends perpendicular to the longitudinal axis (LA) through the center point (C2) of the corresponding laterally intermediate cartridge pocket.

While exit ends (F132c, F132d) of each pair of laterally intermediate pockets (F114c, F114d) may exhibit point symmetry relative to each other about the center point (C2) of the corresponding laterally intermediate cartridge pocket, entry ends (F130c, F130d) of each pair of laterally intermediate pockets (F114c, F114d) do not exhibit point symmetry relative to each other about the center point (C2) of the corresponding laterally intermediate cartridge pocket, such that each pair of laterally intermediate pockets (F114c, F114d) taken as a whole does not exhibit point symmetry relative to each other about the center point (C2) of the corresponding laterally intermediate cartridge pocket. In this regard, the entry end (F130c, F130d) of each laterally intermediate pocket (F114c, F114d) may have a first width (W1) that is asymmetric about the intermediate longitudinal centerline (LG2). For example, the first width (W1) of each entry end (F130c, F130d) may have a first width portion (W1P1) laterally inward of the intermediate longitudinal centerline (LG2), and a second width portion (W1P2) laterally outward of the intermediate longitudinal centerline (LG2) and greater than the first width portion (W1P1). Thus, each pair of laterally intermediate pockets (F114c, F114d) may be asymmetric about each of the intermediate longitudinal centerline (LG2), the corresponding intermediate lateral centerline (LT2), and the center point (C2) of the corresponding laterally intermediate cartridge pocket. Such asymmetry may enable maximizing the sizes of entry ends (F130c, F130d) within the available space provided on anvil surface (F112), thereby improving the ability of entry ends (F130c, F130d) to receive and guide the respective staple legs.

In the example shown, entry ends (F130e, F130f) of laterally outer staple forming pockets (F114e, F114f) extend substantially parallel to the longitudinal axis (LA), while exit ends (F132e, F132f) of laterally outer staple forming pockets (F114e, F114f) extend substantially obliquely relative to the longitudinal axis (LA). In this regard, exit ends (F132e) of proximal, laterally outer staple forming pockets (F114e) are oriented laterally outwardly relative to the longitudinal axis (LA) at a second angle ($\alpha 2$) greater than or otherwise substantially different from the first angle ($\alpha 1$), and exit ends (F132f) of distal, laterally outer staple forming pockets (F114f) are oriented laterally inwardly relative to the longitudinal axis (LA) at the second angle ($\alpha 2$). A medial portion of each laterally outer staple forming pocket (F114e, F114f) located between the respective entry and exit ends (F130e, F130f, F132e, F132f) includes an angled and/or curved sidewall (F136e, F136f) that faces toward the respective entry end (F130e, F130f) and which is longitudinally adjacent to the exit end (F132e, F132f) of the corresponding longitudinally-paired laterally outer staple forming pocket (F114e, F114f). Entry ends (F130e, F130f) are each configured to receive and guide a staple leg in an unformed state longitudinally along the respective concave base surface (F134e, F134f) and toward the respective angled sidewall (F136e, F136f) to be deformed. Exit ends (F132e, F132f) are each configured to guide the staple leg in a deformed state in a direction toward lower cartridge jaw (42) and into clamped tissue (T). The exit end (F132e) of each proximal, laterally outer staple forming pocket (F114e) is laterally adjacent to, and extends substantially parallel to, the exit end (F132f) of the corresponding longitudinally-paired distal, laterally outer staple forming pocket (F114f).

When end effector (40) is closed such that each pair of laterally outer pockets (F114e, F114f) is vertically aligned with a corresponding cartridge pocket (not shown) in a laterally outer row of the staple cartridge that is received within lower cartridge jaw (42), each laterally outer pocket (F114e, F114f) is asymmetrical about an intermediate longitudinal centerline (LG3) that extends parallel to the longitudinal axis (LA) through the center points (C3) of the laterally outer cartridge pockets; and each proximal, laterally outer staple forming pocket (F114e) is asymmetric relative to the corresponding longitudinally-paired distal, laterally outer staple forming pocket (F114f) about a corresponding lateral centerline (LT3) that extends perpendicular to the longitudinal axis (LA) through the center point (C3) of the corresponding laterally outer cartridge pocket.

While exit ends (F132e, F132f) of each pair of laterally outer pockets (F114e, F114f) may exhibit point symmetry relative to each other about the center point (C3) of the corresponding laterally outer cartridge pocket, entry ends (F130e, F130f) of each pair of laterally outer pockets (F114e, F114f) do not exhibit point symmetry relative to each other about the center point (C3) of the corresponding laterally outer cartridge pocket, such that each pair of laterally outer pockets (F114e, F114f) taken as a whole does not exhibit point symmetry relative to each other about the center point (C3) of the corresponding laterally outer cartridge pocket. In this regard, the entry end (F130e, F130f) of each laterally outer pocket (F114e, F114f) may have a second width (W2) greater than the first width (W1) that is asymmetric about the outer longitudinal centerline (LG3). For example, the second width (W2) of each entry end (F130e, F130f) may have a first width portion (W2P1) laterally inward of the outer longitudinal centerline (LG3), and a second width portion (W2P2) laterally outward of the outer longitudinal centerline (LG3) and greater than the first width portion (W2P1). Thus, each pair of laterally outer pockets (F114e, F114f) may be asymmetric about each of the outer longitudinal centerline (LG3), the corresponding outer lateral centerline (LT3), and the center point (C3) of the corresponding laterally outer cartridge pocket. Such asymmetry may enable maximizing the sizes of entry ends (F130e, F130f) within the available space provided on anvil surface (F112), thereby improving the ability of entry ends (F130e, F130f) to receive and guide the respective staple legs.

In the example shown, each proximal, laterally inner staple forming pocket (F114a) is substantially at a same longitudinal position as a corresponding proximal, laterally outer staple forming pocket (F114e), and each distal, laterally inner staple forming pocket (F114b) is substantially at a same longitudinal position as a corresponding distal, laterally outer staple forming pocket (F114f), such that each staple (86a) formed by each pair of laterally inner staple forming pockets (F114a, F114b) may be substantially at a same longitudinal position as the staple (86c) formed by the corresponding pair of laterally outer staple forming pockets (F114e, F114f). However, each proximal, laterally intermediate staple forming pocket (F114c) is substantially offset from each proximal, laterally inner and outer staple forming pocket (F114a, F114e), and each distal, laterally intermediate staple forming pocket (F114d) is substantially offset from each distal, laterally inner and outer staple forming pocket (F114b, F114f), such that each staple (86b) formed by each pair of laterally intermediate staple forming pockets (F114c, F114d) may be substantially offset from the staples (86a, 86c) formed by each pair of laterally inner staple forming pockets (F114a, F114b) and by each pair of outer staple forming pockets (F114e, F114f). For example, each proximal, laterally intermediate staple forming pocket (F114c) may be substantially at a same longitudinal position as corresponding distal, laterally inner and outer staple forming pockets (F114b, F114f), and each distal, laterally intermediate staple forming pocket (F114d) may be substantially at a same longitudinal position as corresponding proximal, laterally inner and outer staple forming pockets (F114a, F114e).

In this manner, the orientations of staple forming pockets (F114a, F114b, F114c, F114d, F114e, F114f) may vary in the lateral direction. More particularly, the orientations may vary from substantially parallel to the longitudinal axis (LA) in the case of each proximal, laterally inner staple forming pocket (F114a), to substantially skewed laterally inwardly toward the longitudinal axis (LA) in the case of the corresponding laterally-adjacent distal, laterally intermediate staple forming pocket (F114d) (e.g., by virtue of the orientation of the respective exit end (F132d)), to substantially skewed laterally outwardly away from the longitudinal axis (LA) in the case of the corresponding laterally-adjacent proximal, laterally outer staple forming pocket (F114e) (e.g., by virtue of the orientation of the respective exit end (F132e)); and may vary from substantially parallel to the longitudinal axis (LA) in the case of each distal, laterally inner staple forming pocket (F114b), to substantially skewed laterally outwardly away from the longitudinal axis (LA) in the case of the corresponding laterally-adjacent proximal, laterally intermediate staple forming pocket (F114c) (e.g., by virtue of the orientation of the respective exit end (F132c)), to substantially skewed laterally inwardly toward the longitudinal axis (LA) in the case of the corresponding laterally-adjacent distal, laterally outer staple forming pocket (F114f) (e.g., by virtue of the orientation of the respective exit end (F132f)).

It will be appreciated that the orientations of staple forming pockets (F114a, F114b, F114c, F114d, F114e, F114f) may vary in the lateral direction in any other suitable manner. For example, each distal, laterally intermediate staple forming pocket (F114d) and distal, laterally outer staple forming pocket (F114f) may be substantially skewed laterally outwardly away from the longitudinal axis (LA), and each proximal, laterally intermediate staple forming pocket (F114c) and proximal, laterally outer staple forming pocket (F114e) may be substantially skewed laterally inwardly toward the longitudinal axis (LA) in an inverse arrangement from that shown.

Figure 10:
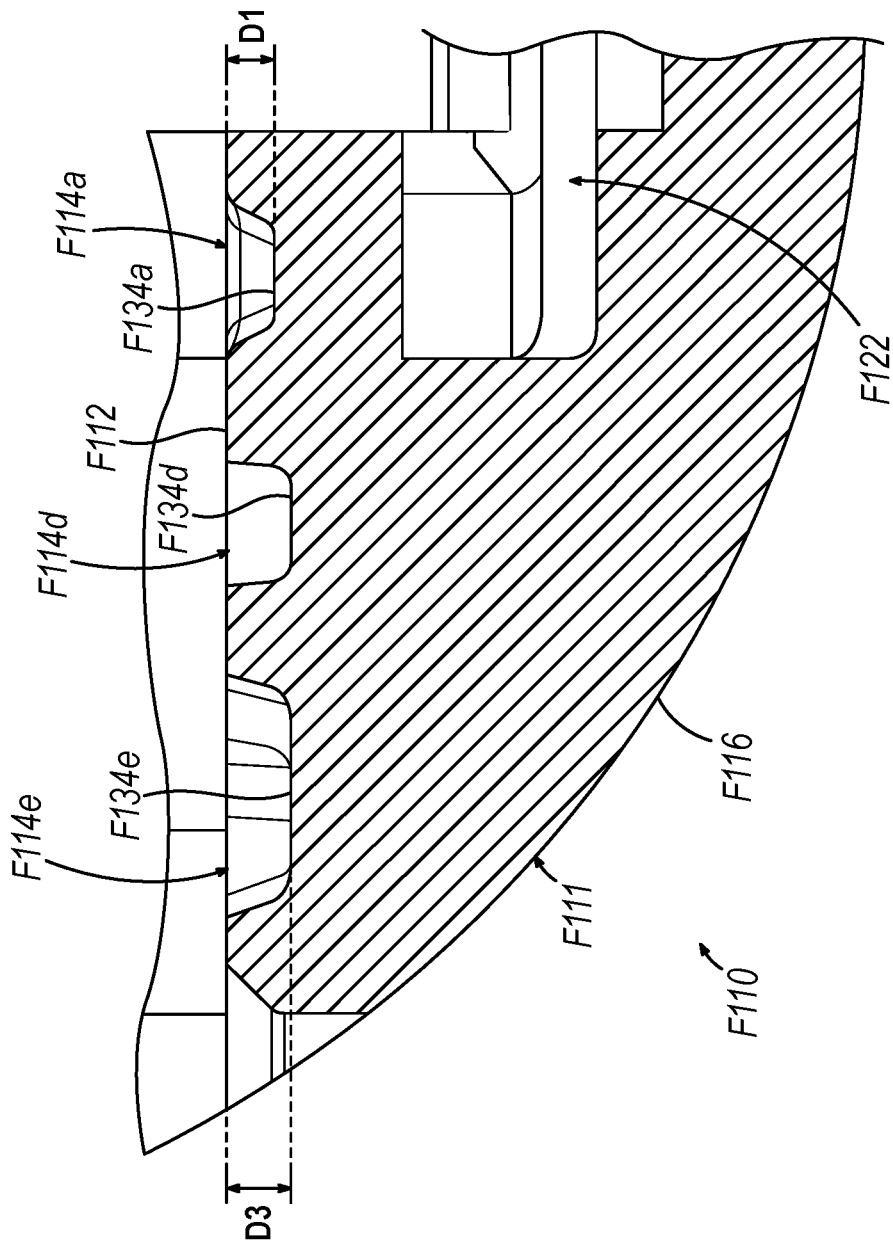
FIG. 10 depicts an end cross-sectional view of the upper anvil jaw of FIG. 7, taken along line 10-10 of FIG. 9.

Referring now to FIG. 10, concave base surfaces (F134a, F134b) of laterally inner staple forming pockets (F114a, F114b) each have a first maximum depth (D1) relative to anvil surface (F112), concave base surfaces (F134c, F134d) of laterally intermediate staple forming pockets (F114c, F114d) each have a second maximum depth (not shown) relative to anvil surface (F112), and concave base surfaces (F134e, F134f) of laterally outer staple forming pockets (F114e, F114f) each have a third maximum depth (D3) relative to anvil surface (F112). As shown, the third maximum depth (D3) is greater than the first maximum depth (D1). In some cases, the second maximum depth may be greater than the first maximum depth (D1) and/or less than the third maximum depth (D3). In addition, or alternatively, the first maximum depth (D1) may be substantially equal to the second maximum depth and/or third maximum depth (D3). The various depths of concave base surfaces (F134a, F134b, F134c, F134d, F134e, F134f) may be selected to provide staples (86a, 86b, 86c) formed by staple forming pockets (F114a, F114b, F114c, F114d, F114e, F114f) with a substantially uniform height in each row. Alternatively, the various depths of concave base surfaces (F134a, F134b, F134c, F134d, F134e, F134f) may be selected to permit the different skews of by staple forming pockets (F114a, F114b, F114c, F114d, F114e, F114f) described above to impart staples (86a, 86b, 86c) with different heights from each other. This may be the case, for example, when the first maximum depth (D1) is substantially equal to each of the second maximum depth and third maximum depth (D3).

Entry ends (F130a, F130b, F130c, F130d, F130e, F130f) of staple forming pockets (F114a, F114b, F114c, F114d, F114e, F114f) may each be oriented downwardly relative to anvil surface (F112) (and/or relative to the longitudinal axis (LA)) in substantially different manners than the corresponding exit ends (F132a, F132b, F132c, F132d, F132e, F132f). For example, as shown in FIG. 11, the entry end (F130e) of each proximal, laterally outer staple forming pocket (F114e) is oriented downwardly relative to anvil surface (F112) (and/or relative to the longitudinal axis (LA)) at a first angle (β1), while the exit end (F132e) of each proximal, laterally outer staple forming pocket (F114e) is oriented downwardly relative to anvil surface (F112) (and/or relative to the longitudinal axis (LA)) at a second angle (β2) greater than or otherwise substantially different from the first angle (β1).

In some versions, the entry end (F130f) of each distal, laterally outer staple forming pocket (F114f) is oriented at the same first angle (31) as the entry end (F130e) of each proximal, laterally outer staple forming pocket (F114e), and/or the exit end (F132f) of each distal, laterally outer staple forming pocket (F114f) is oriented at the same second angle (02) as the exit end (F132f) of each proximal, laterally outer staple forming pocket (F114e). Alternatively, the entry end (F130f) of each distal, laterally outer staple forming pocket (F114f) may be oriented at a first angle substantially different from the first angle (β1) of the entry end (F130e) of each proximal, laterally outer staple forming pocket (F114e), and/or the exit end (F132f) of each distal, laterally outer staple forming pocket (F114f) may be oriented at a second angle substantially different from the second angle (β2) of the exit end (F132f) of each proximal, laterally outer staple forming pocket (F114e). Likewise, any one or more of the entry ends (F130a, F130b, F130c, F130d) of each laterally inner and/or laterally intermediate staple forming pocket (F114a, F114b, F114c, F114d) may be oriented at either the same first angle (31) as the entry end (F130e) of each proximal, laterally outer staple forming pocket (F114e), or a first angle substantially different from the first angle (31) of the entry end (F130e) of each proximal, laterally outer staple forming pocket (F114e); and/or any one or more of the exit ends (F132a, F132b, F132c, F132d) of each laterally inner and/or laterally intermediate staple forming pocket (F114a, F114b, F114c, F114d) may be oriented at either the same second angle (β2) as the exit end (F132e) of each proximal, laterally outer staple forming pocket (F114e), or a second angle substantially different from the second angle (β2) of the exit end (F132e) of each proximal, laterally outer staple forming pocket (F114e).

It will be appreciated that the orientations of entry ends (F130a, F130b, F130c, F130d, F130e, F130f) and exit ends (F132a, F132b, F132c, F132d, F132e, F132f) relative to anvil surface (F112) (and/or relative to the longitudinal axis (LA)), such as first and second angles (β1, β2), may affect the shape of the corresponding formed staple (86a, 86b, 86c), such as a radius of the corresponding formed staple (86a, 86b, 86c) (e.g., when viewed from the side), and may thereby impact springback and/or compression of tissue (T) within the inside area of the corresponding formed staple (86a, 86b, 86c). Thus, the orientations of entry ends (F130a, F130b, F130c, F130d, F130e, F130f) and exit ends (F132a, F132b, F132c, F132d, F132e, F132f) relative to anvil surface (F112) (and/or relative to the longitudinal axis (LA)), such as first and second angles (β1, β2), may be selected to impart the corresponding formed staples (86a, 86b, 86c) with one or more desired shapes.

Figure 11:
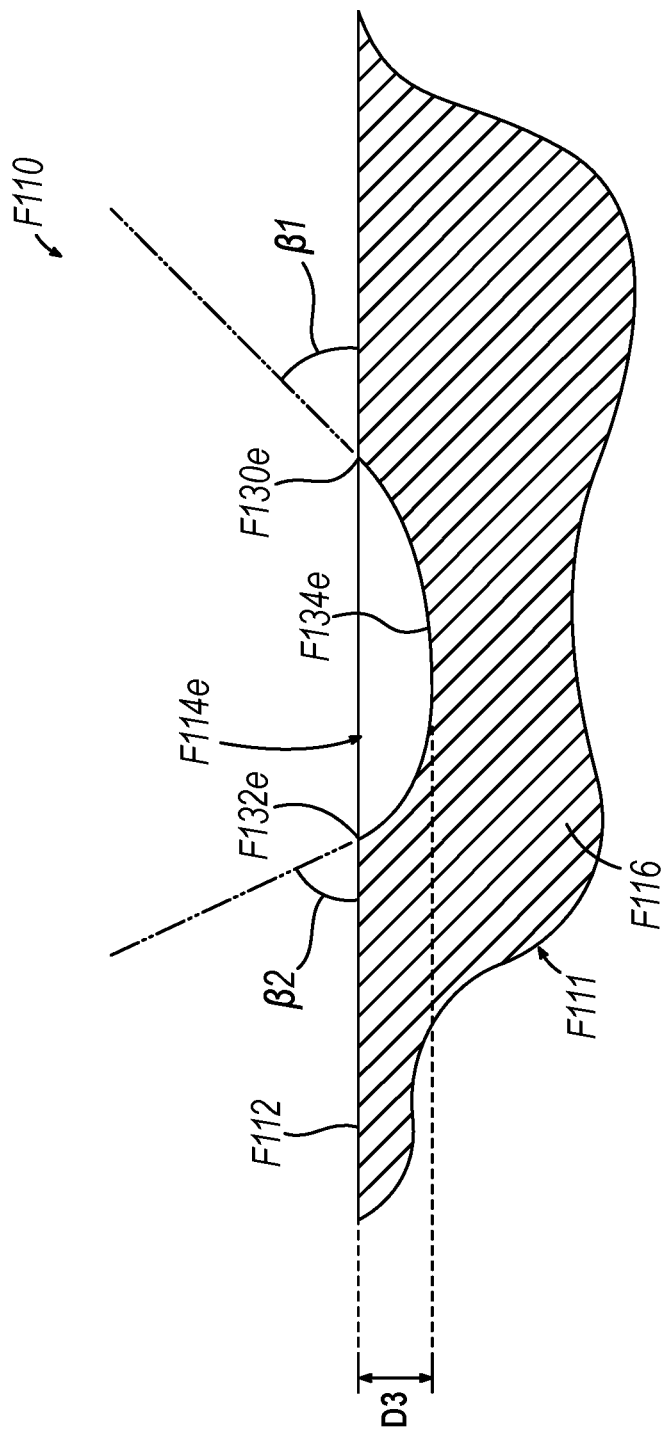
FIG. 11 depicts a cross-sectional view of the upper anvil jaw of FIG. 7, taken along line 11-11 of FIG. 9.

FIG. 11 also shows the third maximum depth (D3) of laterally outer staple forming pockets (F114e, F114f) relative to anvil surface (F112). As noted above, the third maximum depth (D3) may be substantially different from the first maximum depth (D1) of laterally inner staple forming pockets (F114a, F114b) and/or the second maximum depth of laterally intermediate staple forming pockets (F114c, F114d). For example, the third maximum depth (D3) of laterally outer staple forming pockets (F114e, F114f) may be greater than the second maximum depth of laterally intermediate staple forming pockets (F114c, F114d).

In this manner, the depths of staple forming pockets (F114a, F114b, F114c, F114d, F114e, F114f) may vary in the lateral direction. More particularly, the depths may vary from the first maximum depth (D1) in the case of each laterally inner staple forming pocket (F114a, F114b), to the second maximum depth in the case of the corresponding laterally-adjacent, laterally intermediate staple forming pocket (F114d, 114e), to the third maximum depth (D3) in the case of the corresponding laterally-adjacent, laterally outer staple forming pocket (F114e, F114f).

Figure 12:
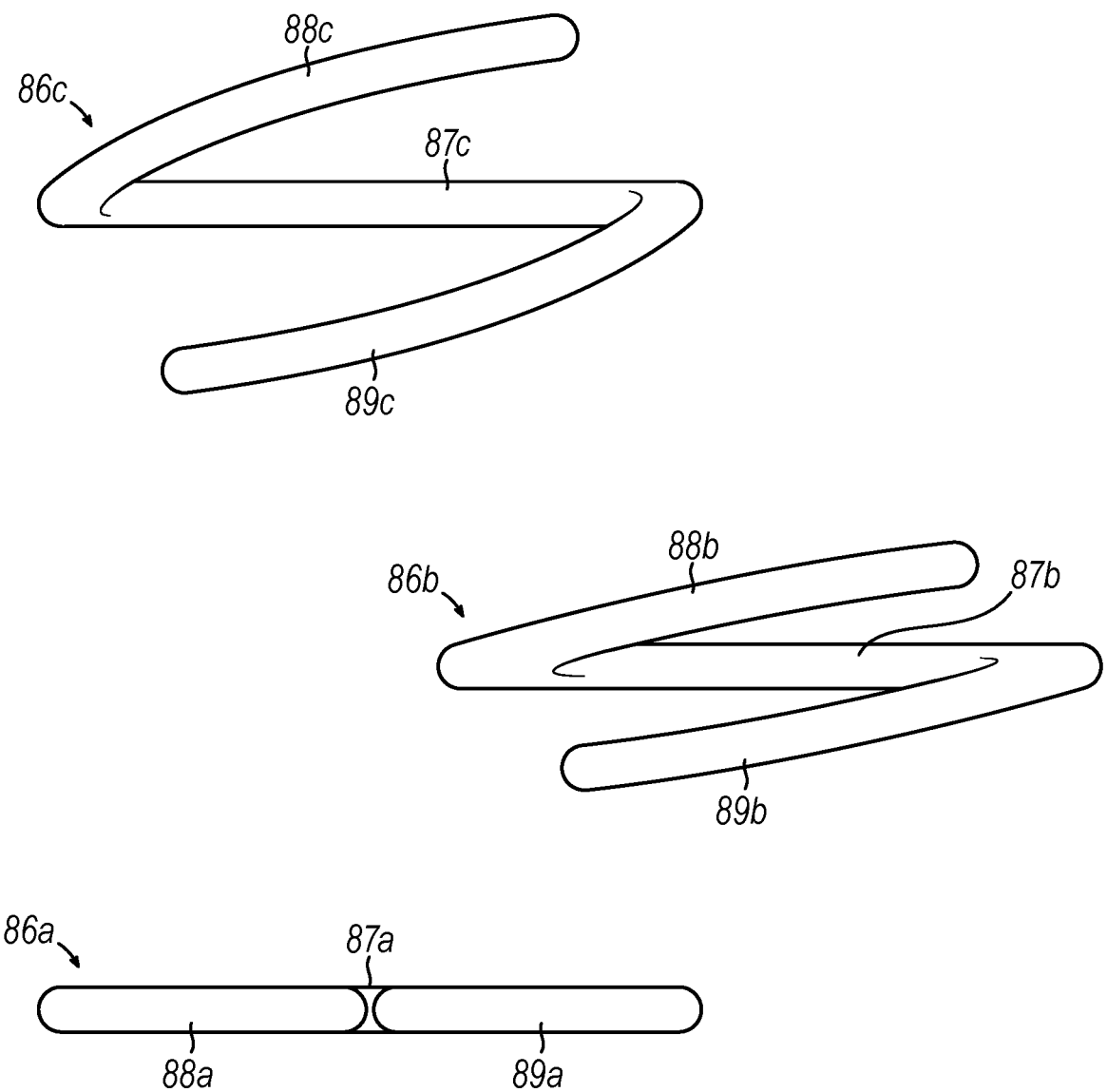
FIG. 12 depicts a top plan view of a plurality of staples formed by the upper anvil jaw of FIG. 7.

As shown in FIG. 12, staple (86a) formed by inner staple forming pockets (F114a, F114b) and staple (86c) formed by outer staple forming pockets (F114e, F114f) are substantially at a same longitudinal position as each other such that staples (86a, 86c) are substantially aligned with each other, while staple (86b) formed by intermediate staple forming pockets (F114c, F114d) is at a substantially different (e.g., nominally different) longitudinal position from staples (86a, 86c) such that staple (86b) is substantially offset from staples (86a, 86c).

As shown, staple (86a) is formed by inner staple forming pockets (F114a, F114b) with a two-dimensional shape (also referred to as a planar shape), while staple (86b) is formed by intermediate staple forming pockets (F114c, F114d) with a three-dimensional shape (also referred to as a non-planar shape) and staple (86c) is formed by outer staple forming pockets (F114e, F114f) with another three-dimensional shape. In this regard, the crown (87a) and both proximal and distal legs (88a, 89a) of staple (86a) all lie in a same plane as each other, with the tips of legs (88a, 89a) laterally aligned with each other. Staple (86a) may be substantially B-shaped in the plane in which crown (87a) and both legs (88a, 89a) reside.

On the other hand, the proximal and distal legs (88b, 89b) of staple (86b) lie in different planes from each other and from crown (87b), with the tips of legs (88b, 89b) laterally offset from each other and from crown (87b) on opposed sides of crown (87b). More particularly, proximal leg (88b) skews laterally outwardly away from the longitudinal axis (LA) at the first angle ($\alpha 1$) relative to crown (87b), and distal leg (89b) skews laterally inwardly toward the longitudinal axis (LA) at the first angle ($\alpha 1$) relative to crown (87b).

Figure 13:
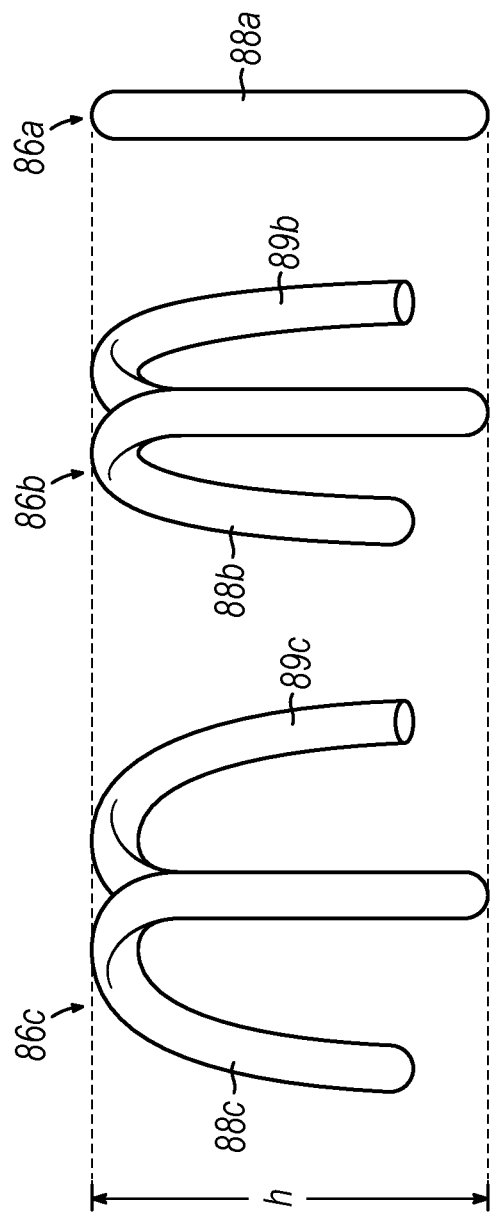
FIG. 13 depicts a front elevational view of the plurality of staples of FIG. 12.

Similarly, the proximal and distal legs (88c, 89c) of staple (86c) lie in different planes from each other and from crown (87c), with the tips of legs (88c, 89c) laterally offset from each other and from crown (87c) on opposed sides of crown (87c). More particularly, proximal leg (88c) skews laterally outwardly away from the longitudinal axis (LA) at the second angle ($\alpha 2$) relative to crown (87c), and distal leg (89c) skews laterally inwardly toward the longitudinal axis (LA) at the second angle ($\alpha 2$) relative to crown (87c). As noted above, the second angle ($\alpha 2$) is greater than the first angle ($\alpha 1$), such that the tips of legs (88c, 89c) may be laterally offset from crown (87c) to a greater degree than that at which the tips of legs (88b, 89b) are laterally offset from crown (87b). In the example shown, the crowns (87a, 87b, 87c) of formed staples (86a, 86b, 86c) are parallel to each other and to the longitudinal axis (LA), such that the crowns (87a, 87b, 87c) may likewise be parallel to the cut line produced by cutting edge (58). In some versions, formed staples (86a, 86b, 86c) may each have a same height (h) as each other in the vertical direction, as shown in FIG. 13. In addition, or alternatively, formed staples (86a, 86b, 86c) may each be formed from a same type of unformed staple (e.g., unformed staple (86)).

Due to the different formed shapes of staples (86a, 86b, 86c), formed staples (86a, 86b, 86c) may provide varying amounts of tissue compression and leak path resistance in the lateral direction, even in cases where formed staples (86a, 86b, 86c) each have a same height as each other. For example, the 2D formed configuration of staple (86a) with non-skewed legs (88a, 89a) may provide a tightest tissue compression and/or a lowest amount of leak path resistance relative to the other staples (86b, 86c); the 3D formed configuration of staple (86b) with legs (88b, 89b) skewed at the first angle ($\alpha 1$) may provide looser tissue compression than staple (86a) and/or a greater amount of leak path resistance than staple (86a); and/or the 3D formed configuration of staple (86c) with legs (88c, 89c) skewed at the second angle ($\alpha 2$) may provide a loosest tissue compression and/or a highest amount of leak path resistance relative to the other staples (86a, 86b). Thus, the rows of formed staples (86a, 86b, 86c) on each side of the cut line produced by cutting edge (58) may collectively achieve both tight tissue compression and good leak path resistance on each side of the cut line.

In this regard, the laterally inner row of formed staples (86a) on each side of the cut line may provide the tightest (e.g., localized) tissue compression near the cut line, while the laterally intermediate row of formed staples (86b) on each side of the cut line may provide more evenly distributed (e.g., less localized) tissue compression farther away from the cut line, and the laterally outer row of formed staples (86c) on each side of the cut line may provide the most evenly distributed (e.g., least localized) tissue compression farthest away from the cut line. Providing the tightest tissue compression immediately adjacent to the cut line via the innermost staples (86a) in this manner (e.g., rather than via the relatively outer staples (86b, 86c)) may ensure an effective seal and/or promote fast healing of the severed tissue (T) along the cut line; while providing the more evenly distributed tissue compression farther away from the cut line via the intermediate and outermost staples (86b, 86c) in this manner (e.g., rather than via the innermost staples (86a)) may relieve strain on the severed tissue (T) and inhibit leakage across the outer and intermediate rows of staples (86b, 86c) toward the inner row of staples (86a).

Figure 14:
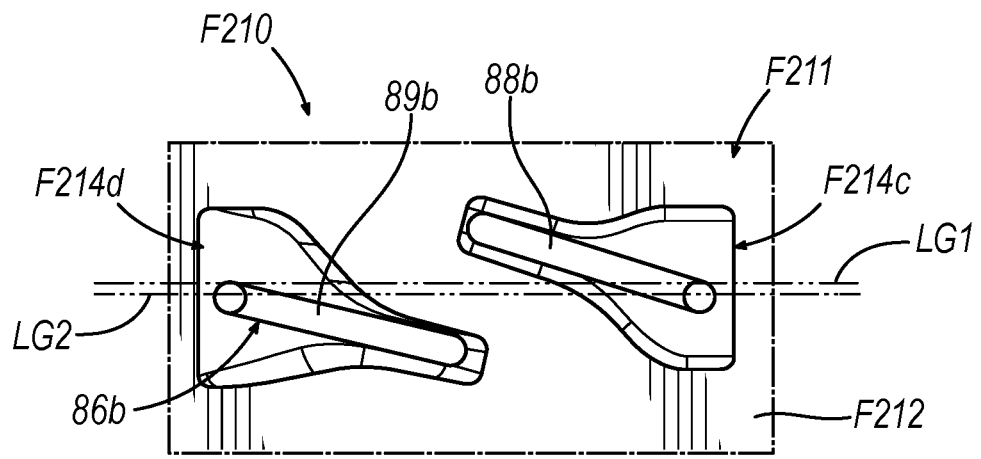
FIG. 14 depicts a bottom plan view of another example of an upper anvil jaw for use with the end effector of FIG. 2 and having a row of staple forming pockets with laterally offset proximal and distal pockets.

III. Example of Anvil Having Row of Staple Forming Pockets with Laterally Offset Proximal and Distal Pockets In some instances, it may be desirable to arrange and configure staple forming pockets (F114a, F114b, F114c, F114d, F1/4e, F114f) of anvil jaw (F110) to further improve the consistency of the formation of at least some staples (86a, 86b, 86c). FIG. 14 shows an example of an anvil jaw (F210) (also referred to as an "anvil") that may provide such capabilities, and that may be incorporated into end effector (40) in place of anvil jaw (44). Anvil jaw (F210) may be similar to anvil jaw (F110) described above, except as otherwise described below. In this regard, anvil jaw (F210) may be configured to pivot relative to cartridge jaw (42) of end effector (40) (or cartridge jaw (42) may be configured to pivot relative to anvil jaw (F210)), to clamp tissue therebetween.

In the example shown, anvil jaw (F210) includes a body (F211) having an interior side that defines an anvil surface (F212) configured to compress tissue and three linear (e.g., straight) rows of staple forming pockets on each side of an anvil slot (not shown), including a laterally inner row of staple forming pockets (not shown) similar to staple forming pockets (F114a, F114b), a laterally intermediate row of staple forming pockets (F214c, F214d), and a laterally outer row of staple forming pockets (not shown) similar to staple forming pockets (F114e, F114f). The laterally inner and outer rows of staple forming pockets may be configured and arranged as shown and described above in connection with FIGS. 7-11.

As shown, staple forming pockets (F214c, F214d) are arranged in longitudinally adjacent pairs such that each pair is configured to receive and deform the legs of a respective staple (86b) and thereby transform the staple (86b) into a formed shape when firing beam (46) is actuated distally. More particularly, each proximal, laterally intermediate staple forming pocket (F214c) is configured to cooperate with the longitudinally adjacent distal, laterally intermediate staple forming pocket (F214d) to provide the resulting staple (86b) with a three-dimensional formed shape in which the crown and each bent leg of the formed staple (86b) lies in a different plane.

The laterally intermediate row of staple forming pockets (F214c, F214d) may be configured and arranged in a manner similar to that shown and described above in connection with FIGS. 7-11, except that in the present version, each proximal, laterally intermediate staple forming pocket (F214c) is laterally offset from the longitudinally adjacent distal, laterally intermediate staple forming pocket (F214d). More particularly, a first longitudinal centerline (LG1) of each proximal, laterally intermediate staple forming pocket (F214c) is laterally offset from (e.g., laterally outward of) a second longitudinal centerline (LG2) of each distal, laterally intermediate staple forming pocket (F214d). In contrast, the proximal and distal laterally inner staple forming pockets may be arranged along a common, laterally inner longitudinal centerline (not shown); and/or the proximal and distal laterally outer staple forming pockets may be arranged along a common, laterally outer longitudinal centerline (not shown).

Due to the lateral offset in the laterally intermediate row of staple forming pockets (F214c, F214d), the proximal staple leg (88b) of each second staple (86b) may contact a surface of the proximal, laterally intermediate staple forming pocket (F214c) earlier, at least by comparison to the proximal laterally, intermediate staple forming pocket (F114c), to assist with ensuring that the proximal staple leg (88b) is angled properly to achieve the desired formation of the second staple (86b).

While each proximal, laterally intermediate staple forming pocket (F214c) is laterally offset from the longitudinally adjacent distal, laterally intermediate staple forming pocket (F214d) in the example shown, in some other versions the proximal and distal laterally intermediate staple forming pockets (F214c, F214d) may be arranged along a common, laterally intermediate longitudinal centerline. In such cases, the proximal and distal laterally inner staple forming pockets may be laterally offset from each other; and/or the proximal and distal laterally outer staple forming pockets may be laterally offset from each other.

Figure 15:
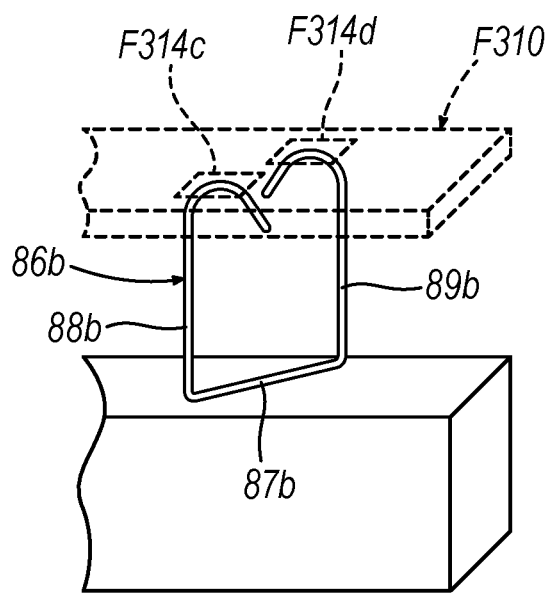
FIG. 15 depicts a schematic view of an anvil having laterally offset proximal and distal staple forming pockets, in conjunction with a staple having a crown that is oriented obliquely relative to the anvil slot.
Figure 16:
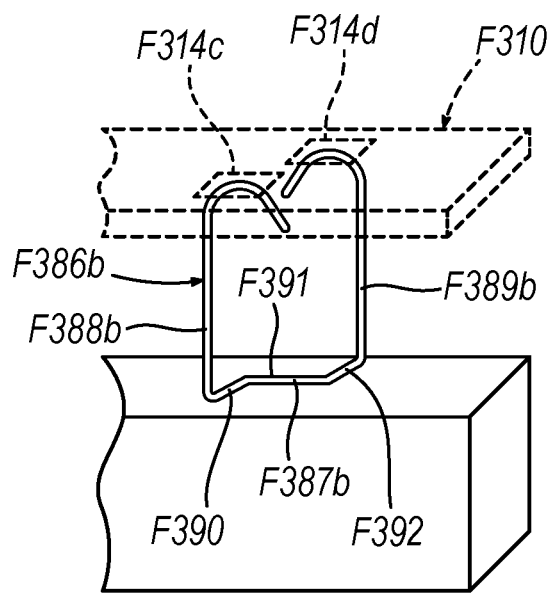
FIG. 16 depicts a schematic view of an anvil having laterally offset proximal and distal staple forming pockets, in conjunction with a staple having a zigzag-shaped crown.

IV. Examples of Staples for Anvil Having Laterally Offset Proximal and Distal Staple Forming Pockets In some instances, it may be desirable to adjust a position and/or shape of a crown (87a, 87b, 87c) of at least some staples (86a, 86b, 86c) to further improve the consistency of the formation of at least some staples (86a, 86b, 86c). FIGS. 15 and 16 schematically show an example of an anvil jaw (F310) (also referred to as an "anvil") that may be incorporated into end effector (40) in place of anvil jaw (44). Anvil jaw (F310) may be similar to anvil jaw (F210) described above, except as otherwise described below. In this regard, anvil jaw (F310) may be configured to pivot relative to cartridge jaw (42) of end effector (40) (or cartridge jaw (42) may be configured to pivot relative to anvil jaw (F310)), to clamp tissue therebetween.

In the example shown, anvil jaw (F310) includes three linear (e.g., straight) rows of staple forming pockets on each side of an anvil slot (not shown), including a laterally inner row of staple forming pockets (not shown) similar to staple forming pockets (F114a, F114b), a laterally intermediate row of staple forming pockets (F314c, F314d), and a laterally outer row of staple forming pockets (not shown) similar to staple forming pockets (F114e, F114f). The laterally inner and outer rows of staple forming pockets may be configured and arranged as shown and described above in connection with FIGS. 7-11.

As shown, staple forming pockets (F314c, F314d) are arranged in longitudinally adjacent pairs such that each pair is configured to receive and deform the legs of a respective staple (86b) and thereby transform the staple (86b) into a formed shape when firing beam (46) is actuated distally. More particularly, each proximal, laterally intermediate staple forming pocket (F314c) is configured to cooperate with the longitudinally adjacent distal, laterally intermediate staple forming pocket (F314d) to provide the resulting staple (86b) with a three-dimensional formed shape in which the crown and each bent leg of the formed staple (86b) lies in a different plane. In the present version, each proximal, laterally intermediate staple forming pocket (F314c) is laterally offset from the longitudinally adjacent distal, laterally intermediate staple forming pocket (F314d).

As shown in FIG. 15, the crown (87b) of each second staple (86b) may be positioned to further improve the consistency of the formation of second staples (86b). More particularly, the crown (87b) of each second staple (86b) may be oriented obliquely relative to the anvil slot, rather than being parallel to the anvil slot, to thereby provide the formed staple (86b) with an enhanced 3D shape.

As shown in FIG. 16, an alternative second staple (F386b) includes a generally zigzag-shaped crown (F387b) and a pair of legs (F388b, F389b). More particularly, the crown (F387b) of each second staple (F386b) includes a proximal segment (F390) oriented obliquely relative to the anvil slot, an intermediate segment (F391) oriented parallel to the anvil slot, and a distal segment (F392) oriented obliquely relative to the anvil slot, to thereby provide the formed staple (F386b) with an enhanced 3D shape.

V. Examples of Asymmetric Staple Patterns

Figure 17:
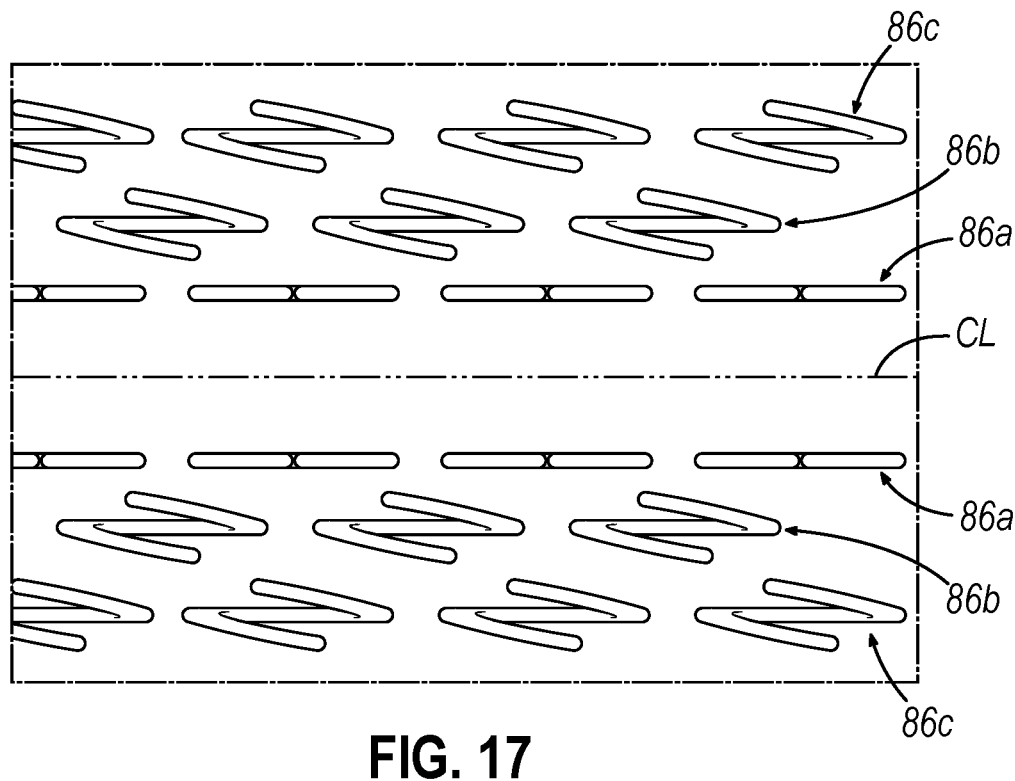
FIG. 17 depicts a top plan view of a plurality of formed staples that are asymmetric relative to a cut line produced by the distal knife portion of FIG. 5.
Figure 18:
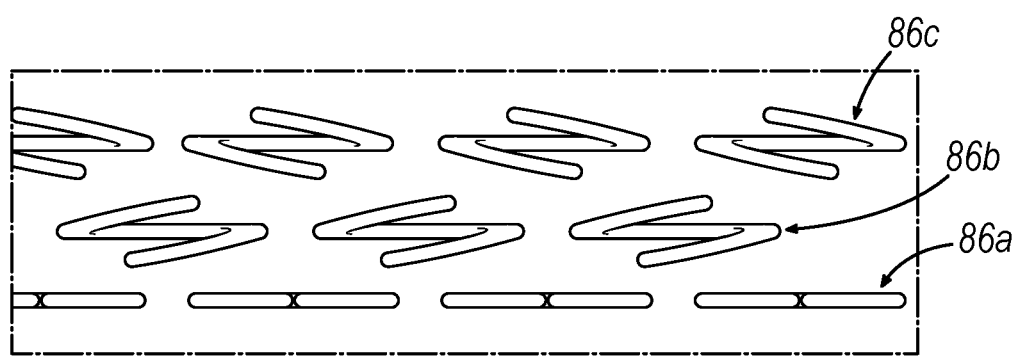
FIG. 18 depicts a top plan view of a plurality of formed staples including a laterally intermediate row of 3D-formed staples that are oriented in an inverted manner relative to a laterally outer row of 3D-formed staples.

In some instances, it may be desirable to adjust the arrangement of staples (86a, 86b, 86c) to further improve the consistency of the formation of at least some staples (86a, 86b, 86c) and/or to further inhibit leakage across the rows of staples (86a, 86b, 86c). FIGS. 17 and 18 show examples of alternative arrangements of staples (86a, 86b, 86c) that may provide such capabilities.

As shown in FIG. 17, staples (86a, 86b, 86c) are asymmetric relative to the cut line (CL) produced by cutting edge (58). More particularly, staples (86b, 86c) are oriented in a uniform manner on both sides of the cut line (CL). It will be appreciated that the arrangement of staples (86a, 86b, 86c) shown in FIG. 17 may be achieved using a modified version of anvil jaw (F110) that will be readily apparent to persons skilled in the art. For example, such a modified version of anvil jaw (F110) may include staple forming pockets that are arranged asymmetrically relative to anvil slot (F122).

As shown in FIG. 18, second staples (86b) are oriented in an inverted manner relative to third staples (86c). It will be appreciated that the arrangement of staples (86a, 86b, 86c) shown in FIG. 18 may be achieved using a modified version of anvil jaw (F110) that will be readily apparent to persons skilled in the art.

VI. Examples of Staple Crowns with Large Compression Areas

Figure 19:
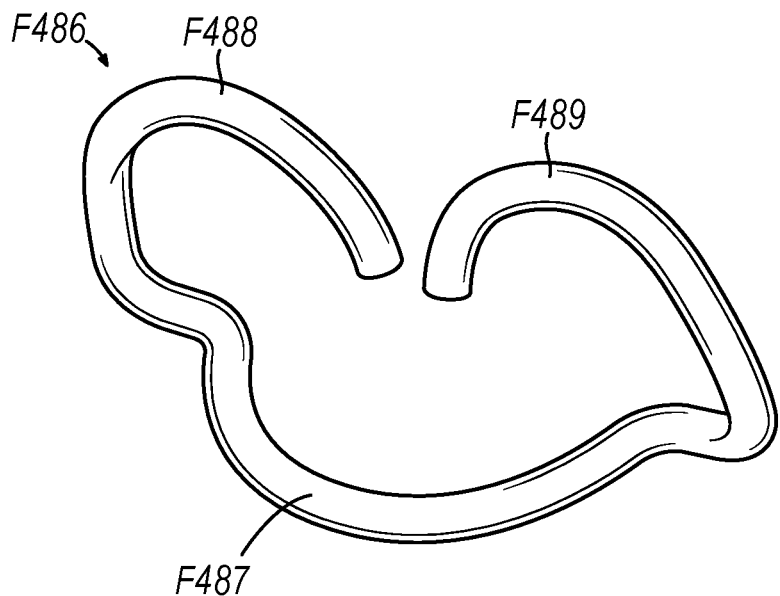
FIG. 19 depicts a perspective view of another example of a staple for use with the end effector of FIG. 2 and having a generally C-shaped crown.
Figure 20:
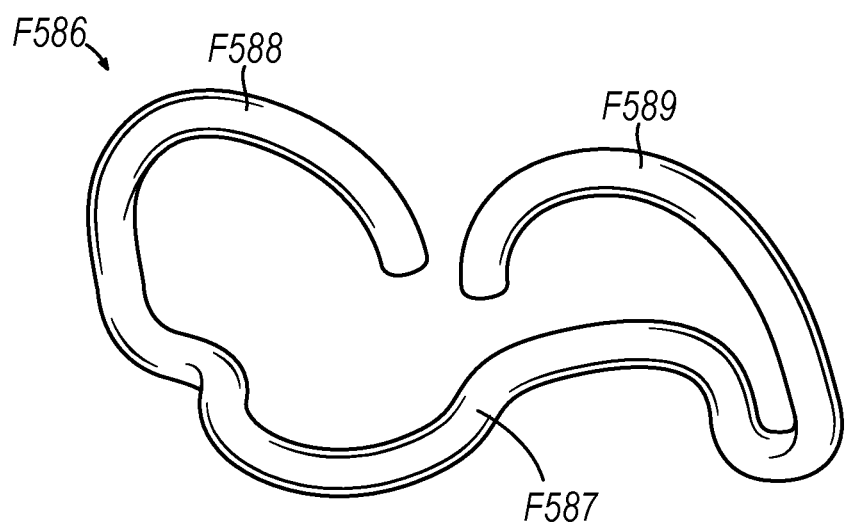
FIG. 20 depicts a perspective view of another example of a staple for use with the end effector of FIG. 2 and having a generally S-shaped crown.

In some instances, it may be desirable to shape a crown (87a, 87b, 87c) of at least some staples (86a, 86b, 86c) to provide an increased compression profile. FIGS. 19 and 20 show examples of staples (F486, F586) that may provide such capabilities.

As shown in FIG. 19, staple (F486) includes a generally C-shaped crown (F487) and a pair of legs (F488, F489). It will be appreciated that C-shaped crown (F487) may be either preformed prior to firing, or formed during firing (e.g., bent from a straight/linear shape).

As shown in FIG. 20, staple (F586) includes a generally S-shaped crown (F587) and a pair of legs (F588, F589). It will be appreciated that S-shaped crown (F587) may be either preformed prior to firing, or formed during firing (e.g., bent from a straight/linear shape).

It will be understood that while the features shown and described above are presented in the context of anvil jaws (F110, F210, F310) for surgical stapler (10), such features may also be applied to staple cartridges configured for use with various other types of surgical staplers, such as linear surgical staplers.

VII. Examples of Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus (F110, F210, F310), comprising: (a) a jaw body (F111, F211) configured to cooperate with an opposing jaw (42) of a surgical stapler (10) to compress, staple, and cut tissue; (b) an anvil surface (F112, F212) defined by the jaw body (F111, F211); (c) an elongate slot (F122) extending through the anvil surface (F112, F212) and along a longitudinal axis (LA) of the jaw body (F111, F211), wherein the elongate slot (F122) is configured to slidably receive a firing driver (46) of the surgical stapler (10); (d) a first longitudinal row of staple forming pockets (F114a, F114b) disposed on the anvil surface (F112, F212) and configured to form a plurality of first staples (86a) ejected from a stapling assembly (70) of the surgical stapler (10) such that first legs (88a, 89a) of each formed first staple (86a) are laterally aligned with each other, and such that a first crown (87a) of each formed first staple (86a) is oriented substantially parallel to the longitudinal axis (LA); and (e) a second longitudinal row of staple forming pockets (F114c, F114d, F214c, F214d, F314c, F314d) disposed on the anvil surface (F112, F212) laterally outwardly of the first longitudinal row of staple forming pockets (F114a, F114b) relative to the longitudinal axis (LA), and configured to form a plurality of second staples (86b) ejected from the stapling assembly (70) of the surgical stapler (10) such that second legs (88b, 89b) of each formed second staple (86b) skew laterally away from a second crown (87b) of the respective formed second staple (86b), and such that the second crown (87b) of each formed second staple (86b) is oriented substantially parallel to the longitudinal axis (LA).

Example 2

The apparatus (F110, F210, F310) of Example 1, wherein the second longitudinal row of staple forming pockets (F114c, F114d, F214c, F214d, F314c, F314d) is arranged in longitudinally adjacent pairs, wherein a first one (F114c, F214c, F314c) of each pair of staple forming pockets (F114c, F114d, F214c, F214d, F314c, F314d) of the second longitudinal row of staple forming pockets (F114c, F114d, F214c, F214d, F314c, F314d) is asymmetric to a second one (F114d, F214d, F314d) of each pair of staple forming pockets (F114c, F114d, F214c, F214d, F314c, F314d).

Example 3

The apparatus (F110, F210, F310) of any of Examples 1 through 2, further comprising a third longitudinal row of staple forming pockets (F114e, F114f) disposed on the anvil surface (F112, F212) and configured to form a plurality of third staples (86c) ejected from the stapling assembly (70) of the surgical stapler (10) such that third legs (88c, 89c) of each formed third staple (86c) skew laterally away from a third crown (87c) of the respective formed third staple (86c), and such that the third crown (87c) of each formed third staple (86c) is oriented substantially parallel to the longitudinal axis (LA).

Example 4

The apparatus (F110, F210, F310) of Example 3, wherein the third longitudinal row of staple forming pockets (F114e, F114f) is disposed on the anvil surface (F112, F212) laterally outwardly of the second longitudinal row of staple forming pockets (F114c, F114d, F214c, F214d, F314c, F314d) relative to the longitudinal axis (LA).

Example 5

The apparatus (F110, F210, F310) of any of Examples 3 through 4, wherein the second longitudinal row of staple forming pockets (F114c, F114d, F214c, F214d, F314c, F314d) is configured to form the plurality of second staples (86b) such that second legs (88b, 89b) of each formed second staple (86b) skew laterally away from the second crown (87b) of the respective formed second staple (86b) at a first angle ($\alpha 1$), wherein the third longitudinal row of staple forming pockets (F114e, F114f) is configured to form the plurality of third staples (86c) such that third legs (88c, 89c) of each formed third staple (86c) skew laterally away from the third crown (87c) of the respective formed third staple (86c) at a second angle ($\alpha 2$) different from the first angle ($\alpha 1$).

Example 6

The apparatus (F110, F210, F310) of Example 5, wherein the second angle ($\alpha 2$) is greater than the first angle ($\alpha 1$).

Example 7

The apparatus (F110, F210, F310) of any of Examples 3 through 6, wherein the third longitudinal row of staple forming pockets (F114e, F114f) is configured to form the plurality of third staples (86c) such that each formed third staple (86c) has a same height as each formed second staple (86b).

Example 8

The apparatus (F110, F210, F310) of any of Examples 3 through 6, wherein the third longitudinal row of staple forming pockets (F114e, F114f) is configured to form the plurality of third staples (86c) such that each formed third staple (86c) has a different height from each formed second staple (86b).

Example 9

The apparatus (F110, F210, F310) of any of Examples 3 through 8, wherein the third longitudinal row of staple forming pockets (F114e, F114f) is configured to form the plurality of third staples (86c) such that each formed third staple (86c) is at a same longitudinal position as a corresponding formed first staple (86a).

Example 10

The apparatus (F110, F210, F310) of any of Examples 3 through 9, wherein the third longitudinal row of staple forming pockets (F114e, F114f) is configured to form the plurality of third staples (86c) such that each formed third staple (86c) is at a different longitudinal position from each formed second staple (86b).

Example 11

The apparatus (F110, F210, F310) of any of Examples 1 through 10, wherein the second longitudinal row of staple forming pockets (F114c, F114d, F214c, F214d, F314c, F314d) is configured to form the plurality of second staples (86b) such that each formed second staple (86b) is at a different longitudinal position from each formed first staple (86a).

Example 12

The apparatus (F110, F210, F310) of any of Examples 1 through 11, wherein the second longitudinal row of staple forming pockets (F114c, F114d, F214c, F214d, F314c, F314d) is configured to form the plurality of second staples (86b) such that each formed second staple (86b) has a same height as each formed first staple (86a).

Example 13

The apparatus (F110, F210, F310) of any of Examples 1 through 11, wherein the second longitudinal row of staple forming pockets (F114c, F114d, F214c, F214d, F314c, F314d) is configured to form the plurality of second staples (86b) such that each formed second staple (86b) has a different height from each formed first staple (86a).

Example 14

The apparatus (F110, F210, F310) of any of Examples 1 through 13, wherein each staple forming pocket (F114c, F114d, F214c, F214d, F314c, F314d) of the second longitudinal row of staple forming pockets (F114c, F114d, F214c, F214d, F314c, F314d) has a same depth relative to the anvil surface (F112, F212) as each staple forming pocket (F114a, F114b) of the first longitudinal row of staple forming pockets (F114a, F114b).

Example 15

The apparatus (F110, F210, F310) of any of Examples 1 through 14, wherein the anvil surface (F112, F212) is planar.

Example 16

An apparatus (F110, F210, F310), comprising: (a) a jaw body (F111, F211) configured to cooperate with an opposing jaw (42) of a surgical stapler (10) to compress, staple, and cut tissue; (b) an anvil surface (F112, F212) defined by the jaw body (F111, F211); (c) an elongate slot (F122) extending through the anvil surface (F112, F212) and along a longitudinal axis (LA) of the jaw body (F111, F211), wherein the elongate slot (F122) is configured to slidably receive a firing driver (46) of the surgical stapler (10); (d) a first longitudinal row of staple forming pockets (F114a, F114b) disposed on the anvil surface (F112, F212), wherein each staple forming pocket (F114a, F114b) of the first longitudinal row of staple forming pockets (F114a, F114b) is oriented substantially parallel to the longitudinal axis (LA) and is configured to form a corresponding staple (86a) with a two-dimensional shape; and (e) a second longitudinal row of staple forming pockets (F114c, F114d, F214c, F214d, F314c, F314d) disposed on the anvil surface (F112, F212), wherein each staple forming pocket (F114c, F114d, F214c, F214d, F314c, F314d) of the second longitudinal row of staple forming pockets (F114c, F114d, F214c, F214d, F314c, F314d) is skewed laterally relative to the longitudinal axis (LA) and is configured to form a corresponding staple (86b) with a three-dimensional shape.

Example 17

The apparatus (F110, F210, F310) of Example 16, wherein the second longitudinal row of staple forming pockets (F114c, F114d, F214c, F214d, F314c, F314d) is disposed on the anvil surface (F112, F212) laterally outwardly of the first longitudinal row of staple forming pockets (F114a, F114b) relative to the longitudinal axis (LA).

Example 18

The apparatus (F110, F210, F310) of any of Examples 16 through 17, wherein at least one staple forming pocket (F114c, F214c, F314c) of the second longitudinal row of staple forming pockets (F114c, F114d, F214c, F214d, F314c, F314d) is skewed laterally outwardly relative to the longitudinal axis (LA), wherein at least one other staple forming pocket (F114d, F214d, F314d) of the second longitudinal row of staple forming pockets (F114c, F114d, F214c, F214d, F314c, F314d) is skewed laterally inwardly relative to the longitudinal axis (LA).

Example 19

The apparatus (F110, F210, F310) of any of Examples 16 through 18, further comprising a third longitudinal row of staple forming pockets (F114e, F114f) disposed on the anvil surface (F112, F212), wherein each staple forming pocket (F114e, F114f) of the third longitudinal row of staple forming pockets (F114e, F114f) is skewed laterally relative to the longitudinal axis (LA) to a different degree than each staple forming pocket (F114c, F114d, F214c, F214d, F314c, F314d) of the second longitudinal row of staple forming pockets (F114c, F114d, F214c, F214d, F314c, F314d).

Example 20

The apparatus (F110, F210, F310) of Example 19, wherein each staple forming pocket (F114e, F114f) of the third longitudinal row of staple forming pockets (F114e, F114f) has a substantially different depth relative to the anvil surface (F112, F212) from each staple forming pocket (F114c, F114d, F214c, F214d, F314c, F314d) of the second longitudinal row of staple forming pockets (F114c, F114d, F214c, F214d, F314c, F314d).

Example 21

The apparatus (F110, F210, F310) of any of Examples 19 through 20, wherein the third longitudinal row of staple forming pockets (F114e, F114f) is disposed on the anvil surface (F112, F212) laterally outwardly of the second longitudinal row of staple forming pockets (F114c, F114d, F214c, F214d, F314c, F314d) relative to the longitudinal axis (LA).

Example 22

The apparatus (F110, F210, F310) of any of Examples 19 through 21, wherein each staple forming pocket (F114c, F114d, F214c, F214d, F314c, F314d) of the second longitudinal row of staple forming pockets (F114c, F114d, F214c, F214d, F314c, F314d) is skewed laterally relative to the longitudinal axis (LA) at a first angle ($\alpha 1$), wherein each staple forming pocket (F114e, F114f) of the third longitudinal row of staple forming pockets (F114e, F114f) is skewed laterally relative to the longitudinal axis (LA) at a second angle ($\alpha 2$) greater than the first angle ($\alpha 1$).

Example 23

The apparatus (F110, F210, F310) of any of Examples 19 through 22, wherein the first longitudinal row of staple forming pockets (F114a, F114b) is arranged in longitudinally adjacent pairs of proximal staple forming pockets (F114a) and distal staple forming pockets (F114b), wherein the second longitudinal row of staple forming pockets (F114c, F114d, F214c, F214d, F314c, F314d) is arranged in longitudinally adjacent pairs of proximal staple forming pockets (F114c, F214c, F314c) and distal staple forming pockets (F114d, F214d, F314d), wherein the third longitudinal row of staple forming pockets (F114e, F114f) is arranged in longitudinally adjacent pairs of proximal staple forming pockets (F114e) and distal staple forming pockets (F114f).

Example 24

The apparatus (F110, F210, F310) of Example 23, wherein each proximal staple forming pocket (F114e) of each longitudinally adjacent pair of the third longitudinal row of staple forming pockets (F114e, F114f) is at a same longitudinal position as a corresponding proximal staple forming pocket (F114a) of a corresponding longitudinally adjacent pair of the first longitudinal row of staple forming pockets (F114a, F114b).

Example 25

The apparatus (F110, F210, F310) of any of Examples 23 through 24, wherein each distal staple forming pocket (F114f) of each longitudinally adjacent pair of the third longitudinal row of staple forming pockets (F114e, F114f) is at a same longitudinal position as a corresponding distal staple forming pocket (F114b) of a corresponding longitudinally adjacent pair of the first longitudinal row of staple forming pockets (F114a, F114b).

Example 26

The apparatus (F110, F210, F310) of any of Examples 23 through 25, wherein each proximal staple forming pocket (F114e) of each longitudinally adjacent pair of the third longitudinal row of staple forming pockets (F114e, F114f) is at a same longitudinal position as a corresponding distal staple forming pocket (F114d, F214d, F314d) of a corresponding longitudinally adjacent pair of the second longitudinal row of staple forming pockets (F114c, F114d, F214c, F214d, F314c, F314d).

Example 27

The apparatus (F110, F210, F310) of any of Examples 23 through 26, wherein each distal staple forming pocket (F114f) of each longitudinally adjacent pair of the third longitudinal row of staple forming pockets (F114e, F114f) is at a same longitudinal position as a corresponding proximal staple forming pocket (F114c, F214c, F314c) of a corresponding longitudinally adjacent pair of the second longitudinal row of staple forming pockets (F114c, F114d, F214c, F214d, F314c, F314d).

Example 28

The apparatus (F110, F210, F310) of any of Examples 16 through 27, wherein the anvil surface (F112, F212) is planar.

Example 29

The apparatus (F110, F210, F310) of any of Examples 16 through 28, wherein at least one staple forming pocket (F114c, F114d, F214c, F214d, F314c, F314d) of the second longitudinal row of staple forming pockets (F114c, F114d, F214c, F214d, F314c, F314d) includes a staple leg entry portion (F130c, F130d) oriented relative to the anvil surface (F112, F212) at a first angle ($\beta 1$), and a staple leg exit portion (F132c, F132d) oriented relative to the anvil surface (F112, F212) at a second angle ($\beta 2$) greater than the first angle ($\beta 1$).

Example 30

The apparatus (F110, F210, F310) of any of Examples 16 through 29, wherein the second longitudinal row of staple forming pockets (F114c, F114d, F214c, F214d, F314c, F314d) is arranged in longitudinally adjacent pairs, wherein a first one (F114c, F214c, F314c) of each pair of staple forming pockets (F114c, F114d, F214c, F214d, F314c, F314d) of the second longitudinal row of staple forming pockets (F114c, F114d, F214c, F214d, F314c, F314d) is asymmetric to a second one (F114d, F214d, F314d) of each pair of staple forming pockets (F114c, F114d, F214c, F214d, F314c, F314d).

Example 31

An apparatus (F110, F210, F310), comprising: (a) a jaw body (F111, F211) configured to cooperate with an opposing jaw (42) of a surgical stapler (10) to compress, staple, and cut tissue; (b) an anvil surface (F112, F212) defined by the jaw body (F111, F211); (c) an elongate slot (F122) extending through the anvil surface (F112, F212) and along a longitudinal axis (LA) of the jaw body (F111, F211), wherein the elongate slot (F122) is configured to slidably receive a firing driver (46) of the surgical stapler (10); (d) a first longitudinal row of staple forming pockets (F114a, F114b) disposed on the anvil surface (F112, F212), wherein each staple forming pocket (F114a, F114b) of the first longitudinal row of staple forming pockets (F114a, F114b) is oriented substantially parallel to the longitudinal axis (LA); and (e) a second longitudinal row of staple forming pockets (F114c, F114d, F214c, F214d, F314c, F314d) disposed on the anvil surface (F112, F212) laterally outwardly of the first longitudinal row of staple forming pockets (F114a, F114b) relative to the longitudinal axis (LA), and arranged in longitudinally adjacent pairs, wherein each pair of staple forming pockets (F114c, F114d, F214c, F214d, F314c, F314d) of the second longitudinal row of staple forming pockets (F114c, F114d, F214c, F214d, F314c, F314d) is asymmetric.

Example 32

The apparatus (F110, F210, F310) of Example 31, wherein each staple forming pocket (F114c, F114d, F214c, F214d, F314c, F314d) of each pair of staple forming pockets (F114c, F114d, F214c, F214d, F314c, F314d) of the second longitudinal row of staple forming pockets (F114c, F114d, F214c, F214d, F314c, F314d) is asymmetric about a corresponding longitudinal centerline (LG2).

Example 33

The apparatus (F110, F210, F310) of any of Examples 31 through 32, wherein each proximal staple forming pocket (F114c, F214c, F314c) of each pair of staple forming pockets (F114c, F114d, F214c, F214d, F314c, F314d) of the second longitudinal row of staple forming pockets (F114c, F114d, F214c, F214d, F314c, F314d) is asymmetric to a corresponding distal staple forming pocket (F114d, F214d, F314d) of the respective pair of staple forming pockets (F114c, F114d, F214c, F214d, F314c, F314d) about a corresponding lateral centerline (LT2).

Example 34

The apparatus (F110, F210, F310) of any of Examples 31 through 33, wherein each staple forming pocket (F114c, F114d, F214c, F214d, F314c, F314d) of the second longitudinal row of staple forming pockets (F114c, F114d, F214c, F214d, F314c, F314d) includes a staple leg entry portion (F130c, F130d) and a staple leg exit portion (F132c, F132d) narrower than the corresponding staple leg entry portion (F130c, F130d).

Example 35

The apparatus (F110, F210, F310) of Example 34, wherein the staple leg entry portion (F130c, F130d) of each staple forming pocket (F114c, F114d, F214c, F214d, F314c, F314d) of the second longitudinal row of staple forming pockets (F114c, F114d, F214c, F214d, F314c, F314d) extends substantially parallel to the longitudinal axis (LA).

Example 36

The apparatus (F110, F210, F310) of any of Examples 34 through 35, wherein the staple leg exit portion (F132c, F132d) of each staple forming pocket (F114c, F114d, F214c, F214d, F314c, F314d) of the second longitudinal row of staple forming pockets (F114c, F114d, F214c, F214d, F314c, F314d) extends substantially obliquely relative to the longitudinal axis (LA).

Example 37

The apparatus (F110, F210, F310) of any of Examples 34 through 36, wherein the staple leg entry portion (F130c, F130d) of at least one staple forming pocket (F114c, F114d, F214c, F214d, F314c, F314d) of the second longitudinal row of staple forming pockets (F114c, F114d, F214c, F214d, F314c, F314d) is oriented relative to the anvil surface (F112, F212) at a first angle ($\beta1$), wherein the staple leg exit portion (F132c, F132d) of the at least one staple forming pocket (F114c, F114d, F214c, F214d, F314c, F314d) of the second longitudinal row of staple forming pockets (F114c, F114d, F214c, F214d, F314c, F314d) is oriented relative to the anvil surface (F112, F212) at a second angle ($\beta2$) different from the first angle ($\beta1$).

Example 38

The apparatus (F110, F210, F310) of Example 37, wherein the second angle ($\beta2$) is greater than the first angle ($\beta1$).

Example 39

The apparatus (F110, F210, F310) of any of Examples 31 through 38, wherein the first longitudinal row of staple forming pockets (F114a, F114b) is arranged in longitudinally adjacent pairs.

Example 40

The apparatus (F110, F210, F310) of Example 39, wherein each proximal staple forming pocket (F114c, F214c, F314c) of each longitudinally adjacent pair of the second longitudinal row of staple forming pockets (F114c, F114d, F214c, F214d, F314c, F314d) is at a same longitudinal position as a corresponding distal staple forming pocket (F114b) of a corresponding longitudinally adjacent pair of the first longitudinal row of staple forming pockets (F114a, F114b).

Example 41

The apparatus (F110, F210, F310) of any of Examples 39 through 40, wherein each distal staple forming pocket (F114d, F214d, F314d) of each longitudinally adjacent pair of the second longitudinal row of staple forming pockets (F114c, F114d, F214c, F214d, F314c, F314d) is at a same longitudinal position as a corresponding proximal staple forming pocket (F114a) of a corresponding longitudinally adjacent pair of the first longitudinal row of staple forming pockets (F114a, F114b).

Example 42

The apparatus (F110, F210, F310) of any of Examples 31 through 41, wherein each staple forming pocket (F114a, F114b) of the first longitudinal row of staple forming pockets (F114a, F114b) has a substantially different depth relative to the anvil surface (F112, F212) from each staple forming pocket (F114c, F114d, F214c, F214d, F314c, F314d) of the second longitudinal row of staple forming pockets (F114c, F114d, F214c, F214d, F314c, F314d).

Example 43

The apparatus (F110, F210, F310) of any of Examples 31 through 42, further comprising a third longitudinal row of staple forming pockets (F114e, F114f) disposed on the anvil surface (F112, F212) laterally outwardly of the second longitudinal row of staple forming pockets (F114c, F114d, F214c, F214d, F314c, F314d) relative to the longitudinal axis (LA), and arranged in longitudinally adjacent pairs.

Example 44

The apparatus (F110, F210, F310) of Example 43, wherein each pair of staple forming pockets (F114e, F114f) of the third longitudinal row of staple forming pockets (F114e, F114f) is asymmetric.

Example 45

The apparatus (F110, F210, F310) of any of Examples 31 through 44, wherein the anvil surface (F112, F212) is planar.

Example 46

An apparatus (F110, F210, F310), comprising: (a) a jaw body (F111, F211) configured to cooperate with an opposing jaw (42) of a surgical stapler (10) to compress, staple, and cut tissue; (b) an anvil surface (F112, F212) defined by the jaw body; (c) an elongate slot (F122) extending through the anvil surface and along a longitudinal axis (LA) of the jaw body, wherein the elongate slot is configured to slidably receive a firing driver (46) of the surgical stapler; (d) a first longitudinal row of staple forming pockets (F114a, F114b) disposed on the anvil surface, wherein the first longitudinal row of staple forming pockets is arranged in longitudinally adjacent pairs, wherein each longitudinally adjacent pair of the first longitudinal row of staple forming pockets is arranged along a common longitudinal centerline; and (e) a second longitudinal row of staple forming pockets (F114c, F114d, F214c, F214d, F314c, F314d) disposed on the anvil surface laterally outwardly of the first longitudinal row of staple forming pockets relative to the longitudinal axis, and arranged in longitudinally adjacent pairs, wherein each proximal staple forming pocket of each longitudinally adjacent pair of the second longitudinal row of staple forming pockets is laterally offset from the corresponding distal staple forming pocket of the respective longitudinally adjacent pair of the second longitudinal row of staple forming pockets.

Example 47

The apparatus of Example 46, wherein the first longitudinal row of staple forming pockets is configured to form a plurality of first staples (86a) ejected from a stapling assembly (70) of the surgical stapler such that first legs (88a, 89a) of each formed first staple are laterally aligned with each other.

Example 48

The apparatus of any of Examples 46 through 47, wherein the second longitudinal row of staple forming pockets is configured to form a plurality of second staples (86b) ejected from the stapling assembly of the surgical stapler such that second legs (88b, 89b) of each formed second staple skew laterally away from a second crown (87b) of the respective formed second staple.

Example 49

The apparatus of Example 48, further comprising the plurality of second staples, wherein the second crown of each second staple is oriented obliquely relative to the elongate slot.

Example 50

The apparatus of Example 48, further comprising the plurality of second staples, wherein the second crown of each second staple is generally zigzag-shaped.

Example 51

The apparatus of Example 50, wherein the second crown of each second staple includes a proximal segment (F390) oriented obliquely relative to the elongate slot, an intermediate segment (F391) oriented parallel to the elongate slot, and a distal segment (F392) oriented obliquely relative to the elongate slot.

Example 52

The apparatus of any of Examples 46 through 51, further comprising a third longitudinal row of staple forming pockets (F114e, F114f) arranged in longitudinally adjacent pairs.

Example 53

The apparatus of Example 52, wherein the third longitudinal row of staple forming pockets is disposed on the anvil surface laterally outwardly of the second longitudinal row of staple forming pockets relative to the longitudinal axis.

Example 54

The apparatus of any of Examples 52 through 53, wherein each longitudinally adjacent pair of the third longitudinal row of staple forming pockets is arranged along a common longitudinal centerline.

Example 55

The apparatus of any of Examples 52 through 54, wherein each proximal staple forming pocket of each longitudinally adjacent pair of the third longitudinal row of staple forming pockets is laterally offset from the corresponding distal staple forming pocket of the respective longitudinally adjacent pair of the third longitudinal row of staple forming pockets.

Example 56

The apparatus of any of Examples 52 through 55, wherein the third longitudinal row of staple forming pockets is configured to form a plurality of third staples (86c) ejected from the stapling assembly of the surgical stapler such that third legs (88c, 89c) of each formed third staple skew laterally away from a third crown (87c) of the respective formed third staple.

Example 57

The apparatus of Example 56, wherein the second and third longitudinal rows of staple forming pockets are configured to form the pluralities of second and third staples, respectively, such that each formed second staple on a first side of the elongate slot is oriented in an inverted manner relative to each formed third staple on the first side of the elongate slot.

Example 58

The apparatus of any of Examples 46 through 57, wherein the staple forming pockets are arranged asymmetrically relative to the elongate slot.

Example 59

The apparatus of any of Examples 46 through 58, wherein each proximal staple forming pocket of each longitudinally adjacent pair of the second longitudinal row of staple forming pockets is laterally outward of the corresponding distal staple forming pocket of the respective longitudinally adjacent pair of the second longitudinal row of staple forming pockets.

Example 60

The apparatus of any of Examples 46 through 59, wherein the anvil surface is planar.

The following clauses also relate to various non-exhaustive ways in which the teachings herein may be combined or applied.

1. An apparatus, comprising:
   (a) a jaw body configured to cooperate with an opposing jaw of a surgical stapler to compress, staple, and cut tissue;
   (b) an anvil surface defined by the jaw body;
   (c) an elongate slot extending through the anvil surface and along a longitudinal axis of the jaw body, wherein the elongate slot is configured to slidably receive a firing driver of the surgical stapler;
   (d) a first longitudinal row of staple forming pockets disposed on the anvil surface and configured to form a plurality of first staples ejected from a stapling assembly of the surgical stapler such that first legs of each formed first staple are laterally aligned with each other; and
   (e) a second longitudinal row of staple forming pockets disposed on the anvil surface laterally outwardly of the first longitudinal row of staple forming pockets relative to the longitudinal axis, and configured to form a plurality of second staples ejected from the stapling assembly of the surgical stapler such that second legs of each formed second staple skew laterally away from a second crown of the respective formed second staple.

2. The apparatus of Clause 1, wherein the second longitudinal row of staple forming pockets is arranged in longitudinally adjacent pairs, wherein a first one of each pair of staple forming pockets of the second longitudinal row of staple forming pockets is asymmetric to a second one of each pair of staple forming pockets.

3. The apparatus of Clause 1, further comprising a third longitudinal row of staple forming pockets disposed on the anvil surface and configured to form a plurality of third staples ejected from the stapling assembly of the surgical stapler such that third legs of each formed third staple skew laterally away from a third crown of the respective formed third staple, and such that the third crown of each formed third staple is oriented substantially parallel to the longitudinal axis.

4. The apparatus of Clause 3, wherein the third longitudinal row of staple forming pockets is disposed on the anvil surface laterally outwardly of the second longitudinal row of staple forming pockets relative to the longitudinal axis.

5. The apparatus of Clause 3, wherein the second longitudinal row of staple forming pockets is configured to form the plurality of second staples such that second legs of each formed second staple skew laterally away from the second crown of the respective formed second staple at a first angle, wherein the third longitudinal row of staple forming pockets is configured to form the plurality of third staples such that third legs of each formed third staple skew laterally away from the third crown of the respective formed third staple at a second angle different from the first angle.

6. The apparatus of Clause 5, wherein the second angle is greater than the first angle.

7. The apparatus of Clause 3, wherein the third longitudinal row of staple forming pockets is configured to form the plurality of third staples such that each formed third staple has a same height as each formed second staple.

8. The apparatus of Clause 3, wherein the third longitudinal row of staple forming pockets is configured to form the plurality of third staples such that each formed third staple has a different height from each formed second staple.

9. The apparatus of Clause 3, wherein the third longitudinal row of staple forming pockets is configured to form the plurality of third staples such that each formed third staple is at a same longitudinal position as a corresponding formed first staple.

10. The apparatus of Clause 3, wherein the third longitudinal row of staple forming pockets is configured to form the plurality of third staples such that each formed third staple is at a different longitudinal position from each formed second staple.

11. The apparatus of Clause 1, wherein the second longitudinal row of staple forming pockets is configured to form the plurality of second staples such that each formed second staple is at a different longitudinal position from each formed first staple.

12. The apparatus of Clause 1, wherein the second longitudinal row of staple forming pockets is configured to form the plurality of second staples such that each formed second staple has a same height as each formed first staple.

13. The apparatus of Clause 1, wherein the second longitudinal row of staple forming pockets is configured to form the plurality of second staples such that each formed second staple has a different height from each formed first staple.

14. The apparatus of Clause 1, wherein each staple forming pocket of the second longitudinal row of staple forming pockets has a same depth relative to the anvil surface as each staple forming pocket of the first longitudinal row of staple forming pockets.

15. The apparatus of Clause 1, wherein each staple forming pocket of the second longitudinal row of staple forming pockets has a different depth relative to the anvil surface from each staple forming pocket of the first longitudinal row of staple forming pockets.

16. The apparatus of Clause 1, wherein the anvil surface is planar.

17. The apparatus of Clause 1, wherein at least one staple forming pocket of the second longitudinal row of staple forming pockets includes a staple leg entry portion oriented relative to the anvil surface at a first angle, and a staple leg exit portion oriented relative to the anvil surface at a second angle greater than the first angle.

18. An apparatus, comprising:
   (a) a jaw body configured to cooperate with an opposing jaw of a surgical stapler to compress, staple, and cut tissue;
   (b) an anvil surface defined by the jaw body;
   (c) an elongate slot extending through the anvil surface and along a longitudinal axis of the jaw body, wherein the elongate slot is configured to slidably receive a firing driver of the surgical stapler;

(d) a first longitudinal row of staple forming pockets disposed on the anvil surface, wherein each staple forming pocket of the first longitudinal row of staple forming pockets is oriented substantially parallel to the longitudinal axis; and (e) a second longitudinal row of staple forming pockets disposed on the anvil surface, wherein each staple forming pocket of the second longitudinal row of staple forming pockets is skewed laterally relative to the longitudinal axis.

19. The apparatus of Clause 18, wherein the second longitudinal row of staple forming pockets is disposed on the anvil surface laterally outwardly of the first longitudinal row of staple forming pockets relative to the longitudinal axis.

20. An apparatus, comprising:

(a) a jaw body configured to cooperate with an opposing jaw of a surgical stapler to compress, staple, and cut tissue;

(b) an anvil surface defined by the jaw body;

(c) an elongate slot extending through the anvil surface and along a longitudinal axis of the jaw body, wherein the elongate slot is configured to slidably receive a firing driver of the surgical stapler;

(d) a first longitudinal row of staple forming pockets disposed on the anvil surface, wherein each staple forming pocket of the first longitudinal row of staple forming pockets is oriented substantially parallel to the longitudinal axis; and (e) a second longitudinal row of staple forming pockets disposed on the anvil surface laterally outwardly of the first longitudinal row of staple forming pockets relative to the longitudinal axis, and arranged in longitudinally adjacent pairs, wherein each pair of staple forming pockets of the second longitudinal row of staple forming pockets is asymmetric.

VIII. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 18/588,147, entitled "Surgical Stapler Cartridge Having Intermediate Raised Tissue Engagement Protrusions," filed Feb. 27, 2024, published as U.S. Pat. Pub. No. 2024/0382197 on Nov. 21, 2024; U.S. patent application Ser. No. 18/588,175, filed Feb. 27, 2024, entitled "Surgical Stapler Cartridge Having Tissue Engagement Protrusions with Enlarged Engagement Surface," published as U.S. Pat. Pub. No. 2024/0382202 on Nov. 21, 2024; U.S. patent application Ser. No. 18/588,206, filed Feb. 27, 2024, entitled "Surgical Stapler Cartridge Having Raised Surface to Promote Buttress Adhesion," published as U.S. Pat. Pub. No. 2024/0382202 on Nov. 21, 2024; U.S. patent application Ser. No. 18/588,240, filed Feb. 27, 2024, entitled "Surgical Stapler Cartridge Having Cartridge Retention Features," issued as U.S. Pat. No. 12,285,170 on Apr. 29, 2024; U.S. patent application Ser. No. 18/588,684, filed Feb. 27, 2024, entitled "Method of Surgical Stapling," published as U.S. Pat. Pub. No. 2024/0350137 on Oct. 24, 2024; and/or U.S. patent application Ser. No. 18/588,094, filed Feb. 27, 2024, entitled "Incompatible Staple Cartridge Use Prevention Features for Surgical Stapler," published as U.S. Pat. Pub. No. 2024/0382201 on Nov. 21, 2024. The disclosure of each of these U.S. patent applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as those made available by Auris Health, Inc. of Redwood City, CA or by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a jaw body configured to cooperate with an opposing jaw of a surgical stapler to compress, staple, and cut tissue;
   (b) an anvil surface defined by the jaw body;
   (c) an elongate slot extending through the anvil surface and along a longitudinal axis of the jaw body, wherein the elongate slot is configured to slidably receive a firing driver of the surgical stapler;
   (d) a first longitudinal row of staple forming pockets disposed on the anvil surface and configured to form a plurality of first staples ejected from a stapling assembly of the surgical stapler such that first legs of each formed first staple are laterally aligned with each other; and
   (e) a second longitudinal row of staple forming pockets disposed on the anvil surface laterally outwardly of the first longitudinal row of staple forming pockets relative to the longitudinal axis, and configured to form a plurality of second staples ejected from the stapling assembly of the surgical stapler such that second legs of each formed second staple skew laterally away from a second crown of the respective formed second staple.

2. The apparatus of claim 1, wherein the second longitudinal row of staple forming pockets is arranged in longitudinally adjacent pairs, wherein a first one of each pair of staple forming pockets of the second longitudinal row of staple forming pockets is asymmetric to a second one of each pair of staple forming pockets.

3. The apparatus of claim 1, further comprising a third longitudinal row of staple forming pockets disposed on the anvil surface and configured to form a plurality of third staples ejected from the stapling assembly of the surgical stapler such that third legs of each formed third staple skew laterally away from a third crown of the respective formed third staple, and such that the third crown of each formed third staple is oriented substantially parallel to the longitudinal axis.

4. The apparatus of claim 3, wherein the third longitudinal row of staple forming pockets is disposed on the anvil surface laterally outwardly of the second longitudinal row of staple forming pockets relative to the longitudinal axis.

5. The apparatus of claim 3, wherein the second longitudinal row of staple forming pockets is configured to form the plurality of second staples such that second legs of each formed second staple skew laterally away from the second crown of the respective formed second staple at a first angle, wherein the third longitudinal row of staple forming pockets is configured to form the plurality of third staples such that third legs of each formed third staple skew laterally away from the third crown of the respective formed third staple at a second angle different from the first angle.

6. The apparatus of claim 5, wherein the second angle is greater than the first angle.

7. The apparatus of claim 3, wherein the third longitudinal row of staple forming pockets is configured to form the plurality of third staples such that each formed third staple has a same height as each formed second staple.

8. The apparatus of claim 3, wherein the third longitudinal row of staple forming pockets is configured to form the plurality of third staples such that each formed third staple has a different height from each formed second staple.

9. The apparatus of claim 3, wherein the third longitudinal row of staple forming pockets is configured to form the plurality of third staples such that each formed third staple is at a same longitudinal position as a corresponding formed first staple.

10. The apparatus of claim 3, wherein the third longitudinal row of staple forming pockets is configured to form the plurality of third staples such that each formed third staple is at a different longitudinal position from each formed second staple.

11. The apparatus of claim 1, wherein the second longitudinal row of staple forming pockets is configured to form the plurality of second staples such that each formed second staple is at a different longitudinal position from each formed first staple.

12. The apparatus of claim 1, wherein the second longitudinal row of staple forming pockets is configured to form the plurality of second staples such that each formed second staple has a same height as each formed first staple.

13. The apparatus of claim 1, wherein the second longitudinal row of staple forming pockets is configured to form the plurality of second staples such that each formed second staple has a different height from each formed first staple.

14. The apparatus of claim 1, wherein each staple forming pocket of the second longitudinal row of staple forming pockets has a same depth relative to the anvil surface as each staple forming pocket of the first longitudinal row of staple forming pockets.

15. The apparatus of claim 1, wherein each staple forming pocket of the second longitudinal row of staple forming pockets has a different depth relative to the anvil surface from each staple forming pocket of the first longitudinal row of staple forming pockets.

16. The apparatus of claim 1, wherein the anvil surface is planar.

17. The apparatus of claim 1, wherein at least one staple forming pocket of the second longitudinal row of staple forming pockets includes a staple leg entry portion oriented relative to the anvil surface at a first angle, and a staple leg exit portion oriented relative to the anvil surface at a second angle greater than the first angle.

18. An apparatus, comprising:
   (a) a jaw body configured to cooperate with an opposing jaw of a surgical stapler to compress, staple, and cut tissue;
   (b) an anvil surface defined by the jaw body;
   (c) an elongate slot extending through the anvil surface and along a longitudinal axis of the jaw body, wherein the elongate slot is configured to slidably receive a firing driver of the surgical stapler;
   (d) a first longitudinal row of staple forming pockets disposed on the anvil surface, wherein each staple forming pocket of the first longitudinal row of staple forming pockets is oriented substantially parallel to the longitudinal axis; and
   (e) a second longitudinal row of staple forming pockets disposed on the anvil surface, wherein each staple forming pocket of the second longitudinal row of staple forming pockets is skewed laterally relative to the longitudinal axis.

19. The apparatus of claim 18, wherein the second longitudinal row of staple forming pockets is disposed on the anvil surface laterally outwardly of the first longitudinal row of staple forming pockets relative to the longitudinal axis.

20. An apparatus, comprising:
(a) a jaw body configured to cooperate with an opposing jaw of a surgical stapler to compress, staple, and cut tissue;
(b) an anvil surface defined by the jaw body;
(c) an elongate slot extending through the anvil surface and along a longitudinal axis of the jaw body, wherein the elongate slot is configured to slidably receive a firing driver of the surgical stapler;
(d) a first longitudinal row of staple forming pockets disposed on the anvil surface, wherein each staple forming pocket of the first longitudinal row of staple forming pockets is oriented substantially parallel to the longitudinal axis; and
(e) a second longitudinal row of staple forming pockets disposed on the anvil surface laterally outwardly of the first longitudinal row of staple forming pockets relative to the longitudinal axis, and arranged in longitudinally adjacent pairs, wherein each pair of staple forming pockets of the second longitudinal row of staple forming pockets is asymmetric.

* * * * *